United States Patent [19]

Yamaguchi et al.

[11] Patent Number: 5,648,233
[45] Date of Patent: Jul. 15, 1997

[54] MODIFIED TUMOR CYTOTOXIC FACTOR (TCF) AND DNA ENCODING SUCH

[75] Inventors: Kyoji Yamaguchi, Oomiya; Nobuyuki Shima, Oyama; Akihiko Murakami, Tochigi; Masaaki Goto, Tochigi; Eisuke Tsuda, Tochigi; Hiroaki Masunaga, Tochigi; Reiko Takahira, Tochigi; Fumiko Oogaki, Utsunomiya; Masatsugu Ueda; Kanji Higashio, both of Kawagoe, all of Japan

[73] Assignee: Snow Brand Milk Products Co., Ltd., Japan

[21] Appl. No.: 290,937

[22] PCT Filed: Dec. 27, 1993

[86] PCT No.: PCT/JP93/01905

§ 371 Date: Sep. 29, 1994

§ 102(e) Date: Sep. 29, 1994

[87] PCT Pub. No.: WO94/14845

PCT Pub. Date: Jul. 7, 1994

[30] Foreign Application Priority Data

Dec. 28, 1992 [JP] Japan .................... 4-359747

[51] Int. Cl.$^6$ .................. C12P 21/06; C12N 1/20; C07K 1/00
[52] U.S. Cl. .......... 435/69.1; 435/69.4; 435/252.3; 435/320.1; 536/23.5; 530/350; 530/395; 530/399
[58] Field of Search ................ 530/350, 395, 530/399; 435/69.1, 69.4, 252.3, 320.1; 536/23.5; 930/120

[56] References Cited

FOREIGN PATENT DOCUMENTS

| 0461560 | 12/1991 | Japan . |
| 0462277 | 12/1991 | Japan . |
| WO94/14845 | 7/1994 | WIPO . |

OTHER PUBLICATIONS

Goto, M. et al.; "Production of Recombinant Human Erythropoietin in Mammalian Cells: Host–Cell Dependency of the Biological Activity of the Cloned Glycoprotein". Bio/Technology, vol. 6, pp. 67–71, Jan. 1988.

Hofmann, R. et al., "Scatter Factor is a Glycoprotein but Glycosylation is not Required for its Activity", Biochimica et Biophysica Acta, 1120, 343–350 (1992).

Yamaguchi et al, 1991 JBC vol. 266 No. 30 pp. 20434–20439.

Dube et al, 1988 vol. 263 No. 33 JBC pp. 17516–17521.

Shima et al 1991 vol. 180 No. 2 Biochem & Biophy Res Comm pp. 1151–1158.

Weidner et al 1991 vol. 88 PNAS USA pp. 7001–7005.

Rubin et al 1991 vol. 88 pp. 415–419 PNAS.

Primary Examiner—Garnette D. Draper
Attorney, Agent, or Firm—Testa, Hurwitz & Thibeault, LLP

[57] ABSTRACT

Modified TCF in which one or more amino-acid residues of the wild type TCF responsible for glycosylation are substituted or deleted so that at least one N-linked oligosaccharide chain is removed. The modified TCFs have a longer biological half-lives without loss of their biological activities. The modified TCFs are therapeutically important as agents for liver diseases or as anti-cancer drugs.

11 Claims, 11 Drawing Sheets

Met Trp Val Thr Lys Leu Leu Pro Ala Leu Leu Leu Gln His Val Leu
Leu His Leu Leu Leu Leu Pro Ile Ala Ile Pro Tyr Ala Glu Gly Gln
Arg Lys Arg Arg Asn Thr Ile His Glu Phe Lys Lys Ser Ala Lys Thr
Thr Leu Ile Lys Ile Asp Pro Ala Leu Lys Ile Lys Thr Lys Lys Val
Asn Thr Ala Asp Gln Cys Ala Asn Arg Cys Thr Arg Asn Lys Gly Leu
Pro Phe Thr Cys Lys Ala Phe Val Phe Asp Lys Ala Arg Lys Gln Cys
Leu Trp Phe Pro Phe Asn Ser Met Ser Ser Gly Val Lys Lys Glu Phe
Gly His Glu Phe Asp Leu Tyr Glu Asn Lys Asp Tyr Ile Arg Asn Cys
Ile Ile Gly Lys Gly Arg Ser Tyr Lys Gly Thr Val Ser Ile Thr Lys
Ser Gly Ile Lys Cys Gln Pro Trp Ser Ser Met Ile Pro His Glu His
Ser Tyr Arg Gly Lys Asp Leu Gln Glu Asn Tyr Cys Arg Asn Pro Arg
Gly Glu Glu Gly Gly Pro Trp Cys Phe Thr Ser Asn Pro Glu Val Arg
Tyr Glu Val Cys Asp Ile Pro Gln Cys Ser Glu Val Glu Cys Met Thr
Cys Asn Gly Glu Ser Tyr Arg Gly Leu Met Asp His Thr Glu Ser Gly
Lys Ile Cys Gln Arg Trp Asp His Gln Thr Pro His Arg His Lys Phe
Leu Pro Glu Arg Tyr Pro Asp Lys Gly Phe Asp Asp Asn Tyr Cys Arg
Asn Pro Asp Gly Gln Pro Arg Pro Trp Cys Tyr Thr Leu Asp Pro His
Thr Arg Trp Glu Tyr Cys Ala Ile Lys Thr Cys Ala Asp Asn Thr Met
Asn Asp Thr Asp Val Pro Leu Glu Thr Thr Glu Cys Ile Gln Gly Gln
Gly Glu Gly Tyr Arg Gly Thr Val Asn Thr Ile Trp Asn Gly Ile Pro
Cys Gln Arg Trp Asp Ser Gln Tyr Pro His Glu His Asp Met Thr Pro
Glu Asn Phe Lys Cys Lys Asp Leu Arg Glu Asn Tyr Cys Arg Asn Pro
Asp Gly Ser Glu Ser Pro Trp Cys Phe Thr Thr Asp Pro Asn Ile Arg
Val Gly Tyr Cys Ser Gln Ile Pro Asn Cys Asp Met Ser His Gly Gln
Asp Cys Tyr Arg Gly Asn Gly Lys Asn Tyr Met Gly Asn Leu Ser Gln
Thr Arg Ser Gly Leu Thr Cys Ser Met Trp Asp Lys Asn Met Glu Asp
Leu His Arg His Ile Phe Trp Glu Pro Asp Ala Ser Lys Leu Asn Glu
Asn Tyr Cys Arg Asn Pro Asp Asp Asp Ala His Gly Pro Trp Cys Tyr
Thr Gly Asn Pro Leu Ile Pro Trp Asp Tyr Cys Pro Ile Ser Arg Cys
Glu Gly Asp Thr Thr Pro Thr Ile Val Asn Leu Asp His Pro Val Ile
Ser Cys Ala Lys Thr Lys Gln Leu Arg Val Val Asn Gly Ile Pro Thr
Arg Thr Asn Ile Gly Trp Met Val Ser Leu Arg Tyr Arg Asn Lys His
Ile Cys Gly Gly Ser Leu Ile Lys Glu Ser Trp Val Leu Thr Ala Arg
Gln Cys Phe Pro Ser Arg Asp Leu Lys Asp Tyr Glu Ala Trp Leu Gly
Ile His Asp Val His Gly Arg Gly Asp Glu Lys Cys Lys Gln Val Leu
Asn Val Ser Gln Leu Val Tyr Gly Pro Glu Gly Ser Asp Leu Val Leu
Met Lys Leu Ala Arg Pro Ala Val Leu Asp Asp Phe Val Ser Thr Ile
Asp Leu Pro Asn Tyr Gly Cys Thr Ile Pro Glu Lys Thr Ser Cys Ser
Val Tyr Gly Trp Gly Tyr Thr Gly Leu Ile Asn Tyr Asp Gly Leu Leu
Arg Val Ala His Leu Tyr Ile Met Gly Asn Glu Lys Cys Ser Gln His
His Arg Gly Lys Val Thr Leu Asn Glu Ser Glu Ile Cys Ala Gly Ala
Glu Lys Ile Gly Ser Gly Pro Cys Glu Gly Asp Tyr Gly Gly Pro Leu
Val Cys Glu Gln His Lys Met Arg Met Val Leu Gly Val Ile Val Pro
Gly Arg Gly Cys Ala Ile Pro Asn Arg Pro Gly Ile Phe Val Arg Val
Ala Tyr Tyr Ala Lys Trp Ile His Lys Ile Ile Leu Thr Tyr Lys Val
Pro Gln Ser

FIG. 1

```
---------- ---------- ---------- ---------- ---TAGGCAC
TGACTCCGAA CAGGATTCTT TCACCCAGGC ATCTCCTCCA GAGGGATCCG
CCAGCCCGTC CAGCAGCACC ATGTGGGTGA CCAAACTCCT GCCAGCCCTG
CTGCTGCAGC ATGTCCTCCT GCATCTCCTC CTGCTCCCCA TCGCCATCCC
CTATGCAGAG GGACAAAGGA AAAGAAGAAA TACAATTCAT GAATTCAAAA
AATCAGCAAA GACTACCCTA ATCAAAARAG ATCCAGCACT GAAGATAAAA
ACCAAAAAAG TGAATACTGC AGACCAATGT GCTAATAGAT GTACTAGGAA
TAAAGGACTT CCATTCACTT GCAAGGCTTT TGTTTTTGAT AAAGCAAGAA
AACAATGCCT CTGGTTCCCC TTCAATAGCA TGTCAAGTGG AGTGAAAAAA
GAATTTGGCC ATGAATTTGA CCTCTATGAA AACAAAGACT ACATTAGAAA
CTGCATCATT GGTAAAGGAC GCAGCTACAA GGAACAGTA TCTATCACTA
AGAGTGGCAT CAAATGTCAG CCCTGGAGTT CCATGATACC ACACGAACAC
AGCTATCGGG GTAAAGACCT ACAGGAAAAC TACTGTCGAA ATCCTCGAGG
GGAAGAAGGG GGACCCTGGT GTTTCACAAG CAATCCAGAG GTACGCTACG
AAGTCTGTGA CATTCCTCAG TGTTCAGAAG TTGAATGCAT GACCTGCAAT
GGGGAGAGTT ATCGAGGTCT CATGGATCAT ACAGAATCAG GCAAGATTTG
TCAGCGCTGG GATCATCAGA CACCACACCG GCACAAATTC TTGCCTGAAA
GATATCCCGA CAAGGGCTTT GATGATAATT ATTGCCGCAA TCCCGATGGC
CAGCCGAGGC CATGGTGCTA TACTCTTGAC CCTCACACCC GCTGGGAGTA
CTGTGCAATT AAAACATGCG CTGACAATAC TATGAATGAC ACTGATGTTC
CTTTGGAAAC AACTGAATGC ATCCAAGGTC AAGGAGAAGG CTACAGGGGC
ACTGTCAATA CCATTTGGAA TGGAATTCCA TGTCAGCGTT GGGATTCTCA
GTATCCTCAC GAGCATGACA TGACTCCTGA AAATTTCAAG TGCAAGGACC
TACGAGAAAA TTACTGCCGA AATCCAGATG GGTCTGAATC ACCCTGGTGT
TTTACCACTG ATCCAAACAT CCGAGTTGGC TACTGCTCCC AAATTCCAAA
CTGTGATATG TCACATGGAC AAGATTGTTA TCGTGGGAAT GGCAAAAATT
ATATGGGCAA CTTATCCCAA ACAAGATCTG GACTAACATG TTCAATGTGG
GACAAGAACA TGGAAGACTT ACATCGTCAT ATCTTCTGGG AACCAGATGC
AAGTAAGCTG AATGAGAATT ACTGCCGAAA TCCAGATGAT GATGCTCATG
GACCCTGGTG CTACACGGGA AATCCACTCA TTCCTTGGGA TTATTGCCCT
ATTTCTCGTT GTGAAGGTGA TACCACACCT ACAATAGTCA ATTTAGACCA
TCCCGTAATA TCTTGTGCCA AAACGAAACA ATTGCGAGTT GTAAATGGGA
TTCCAACACG AACAAACATA GGATGGATGG TTAGTTTGAG ATACAGAAAT
AAACATATCT GCGGAGGATC ATTGATAAAG GAGAGTTGGG TTCTTACTGC
ACGACAGTGT TTCCCTTCTC GAGACTTGAA AGATTATGAA GCTTGGCTTG
GAATTCATGA TGTCCACGGA AGAGGAGATG AGAAATGCAA ACAGGTTCTC
AATGTTTCCC AGCTGGTATA TGGCCCTGAA GGATCAGATC TGGTTTTAAT
GAAGCTTGCC AGGCCTGCTG TCCTGGATGA TTTTGTTAGT ACGATTGATT
TACCTAATTA TGGATGCACA ATTCCTGAAA AGACCAGTTG CAGTGTTTAT
GGCTGGGGCT ACACTGGATT GATCAACTAT GATGGCCTAT TACGAGTGGC
ACATCTCTAT ATAATGGAAA ATGAGAAATG CAGCCAGCAT CATCGAGGGA
AGGTGACTCT GAATGAGTCT GAAATATGTG CTGGGGCTGA AAAGATTGGA
TCAGGACCAT GTGAGGGGA TTATGGTGGC CCACTTGTTT GTGAGCAACA
TAAAATGAGA ATGGTTCTTG GTGTCATTGT TCCTGGTCGT GGATGTGCCA
TTCCAAATCG TGCTGGTATT TTTGTCCGAG TCGCATATTA TGCAAAATGG
ATACACAAAA TTATTTTAAC ATATAAGGTA CCACAGTCAT AGCTGAAGTA
AGTGTGTCTG AAGCACCCAC CAATACAACT GT
```

FIG. 2

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 723 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:1:

```
Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
                20                  25                  30
```

```
Arg Lys Arg Arg Asn Thr Ile His Glu Phe Lys Lys Ser Ala Lys Thr
         35                  40                  45
Thr Leu Ile Lys Ile Asp Pro Ala Leu Lys Ile Lys Thr Lys Lys Val
     50                  55                  60
Asn Thr Ala Asp Gln Cys Ala Asn Arg Cys Thr Arg Asn Lys Gly Leu
 65                  70                  75                  80
Pro Phe Thr Cys Lys Ala Phe Val Phe Asp Lys Ala Arg Lys Gln Cys
                 85                  90                  95
Leu Trp Phe Pro Phe Asn Ser Met Ser Ser Gly Val Lys Lys Glu Phe
                100                 105                 110
Gly His Glu Phe Asp Leu Tyr Glu Asn Lys Asp Tyr Ile Arg Asn Cys
             115                 120                 125
Ile Ile Gly Lys Gly Arg Ser Tyr Lys Gly Thr Val Ser Ile Thr Lys
         130                 135                 140
Ser Gly Ile Lys Cys Gln Pro Trp Ser Ser Met Ile Pro His Glu His
145                 150                 155                 160
Ser Tyr Arg Gly Lys Asp Leu Gln Glu Asn Tyr Cys Arg Asn Pro Arg
                165                 170                 175
Gly Glu Glu Gly Gly Pro Trp Cys Phe Thr Ser Asn Pro Glu Val Arg
             180                 185                 190
Tyr Glu Val Cys Asp Ile Pro Gln Cys Ser Glu Val Glu Cys Met Thr
         195                 200                 205
Cys Asn Gly Glu Ser Tyr Arg Gly Leu Met Asp His Thr Glu Ser Gly
210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
             260                 265                 270
Thr Arg Trp Glu Tyr Cys Ala Ile Lys Thr Cys Ala Asp Asn Thr Met
         275                 280                 285
Asn Asp Thr Asp Val Pro Leu Glu Thr Thr Glu Cys Ile Gln Gly Gln
290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
             340                 345                 350
Asp Gly Ser Glu Ser Pro Trp Cys Phe Thr Thr Asp Pro Asn Ile Arg
         355                 360                 365
Val Gly Tyr Cys Ser Gln Ile Pro Asn Cys Asp Met Ser His Gly Gln
370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
             420                 425                 430
Asn Tyr Cys Arg Asn Pro Asp Asp Asp Ala His Gly Pro Trp Cys Tyr
         435                 440                 445
Thr Gly Asn Pro Leu Ile Pro Trp Asp Tyr Cys Pro Ile Ser Arg Cys
450                 455                 460
```

```
Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
                580                 585                 590

Asp Leu Pro Asn Tyr Gly Cys Thr Ile Pro Glu Lys Thr Ser Cys Ser
            595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser
```

( 2 ) INFORMATION FOR SEQ ID NO:2:

( i ) SEQUENCE CHARACTERISTICS:
      ( A ) LENGTH: 723 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:2:

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
```

|     |     |     |     |  85 |     |     |     |     |  90 |     |     |     |  95 |     |
|---|---|---|---|---|---|---|---|---|---|---|---|---|---|---|
| Leu | Trp | Phe | Pro 100 | Phe | Asn | Ser | Met | Ser 105 | Ser | Gly | Val | Lys | Lys 110 | Glu | Phe |
| Gly | His | Glu 115 | Phe | Asp | Leu | Tyr | Glu 120 | Asn | Lys | Asp | Tyr | Ile 125 | Arg | Asn | Cys |
| Ile | Ile | Gly 130 | Lys | Gly | Arg | Ser | Tyr 135 | Lys | Gly | Thr | Val | Ser 140 | Ile | Thr | Lys |
| Ser 145 | Gly | Ile | Lys | Cys | Gln 150 | Pro | Trp | Ser | Ser | Met 155 | Ile | Pro | His | Glu | His 160 |
| Ser | Tyr | Arg | Gly | Lys 165 | Asp | Leu | Gln | Glu | Asn 170 | Tyr | Cys | Arg | Asn | Pro 175 | Arg |
| Gly | Glu | Glu | Gly 180 | Gly | Pro | Trp | Cys | Phe 185 | Thr | Ser | Asn | Pro | Glu 190 | Val | Arg |
| Tyr | Glu | Val 195 | Cys | Asp | Ile | Pro | Gln 200 | Cys | Ser | Glu | Val | Glu 205 | Cys | Met | Thr |
| Cys | Asn 210 | Gly | Glu | Ser | Tyr | Arg 215 | Gly | Leu | Met | Asp | His 220 | Thr | Glu | Ser | Gly |
| Lys 225 | Ile | Cys | Gln | Arg | Trp 230 | Asp | His | Gln | Thr | Pro 235 | His | Arg | His | Lys | Phe 240 |
| Leu | Pro | Glu | Arg | Tyr 245 | Pro | Asp | Lys | Gly | Phe 250 | Asp | Asp | Asn | Tyr | Cys 255 | Arg |
| Asn | Pro | Asp | Gly 260 | Gln | Pro | Arg | Pro | Trp 265 | Cys | Tyr | Thr | Leu | Asp 270 | Pro | His |
| Thr | Arg | Trp 275 | Glu | Tyr | Cys | Ala | Ile 280 | Lys | Thr | Cys | Ala | Asp 285 | Asn | Thr | Met |
| Asn | Asp 290 | Thr | Asp | Val | Pro | Leu 295 | Glu | Thr | Thr | Glu | Cys 300 | Ile | Gln | Gly | Gln |
| Gly 305 | Glu | Gly | Tyr | Arg | Gly 310 | Thr | Val | Asn | Thr | Ile 315 | Trp | Asn | Gly | Ile | Pro 320 |
| Cys | Gln | Arg | Trp | Asp 325 | Ser | Gln | Tyr | Pro | His 330 | Glu | His | Asp | Met | Thr 335 | Pro |
| Glu | Asn | Phe | Lys 340 | Cys | Lys | Asp | Leu | Arg 345 | Glu | Asn | Tyr | Cys | Arg 350 | Asn | Pro |
| Asp | Gly | Ser 355 | Glu | Ser | Pro | Trp | Cys 360 | Phe | Thr | Thr | Asp | Pro 365 | Asn | Ile | Arg |
| Val | Gly 370 | Tyr | Cys | Ser | Gln | Ile 375 | Pro | Asn | Cys | Asp | Met 380 | Ser | His | Gly | Gln |
| Asp 385 | Cys | Tyr | Arg | Gly | Asn 390 | Gly | Lys | Asn | Tyr | Met 395 | Gly | Asn | Leu | Ser | Gln 400 |
| Thr | Arg | Ser | Gly | Leu 405 | Thr | Cys | Ser | Met | Trp 410 | Asp | Lys | Asn | Met | Glu 415 | Asp |
| Leu | His | Arg | His 420 | Ile | Phe | Trp | Glu | Pro 425 | Asp | Ala | Ser | Lys | Leu 430 | Asn | Glu |
| Asn | Tyr | Cys 435 | Arg | Asn | Pro | Asp | Asp 440 | Asp | Ala | His | Gly | Pro 445 | Trp | Cys | Tyr |
| Thr | Gly 450 | Asn | Pro | Leu | Ile | Pro 455 | Trp | Asp | Tyr | Cys | Pro 460 | Ile | Ser | Arg | Cys |
| Glu 465 | Gly | Asp | Thr | Thr | Pro 470 | Thr | Ile | Val | Asn | Leu 475 | Asp | His | Pro | Val | Ile 480 |
| Ser | Cys | Ala | Lys | Thr 485 | Lys | Gln | Leu | Arg | Val 490 | Val | Asn | Gly | Ile | Pro 495 | Thr |
| Arg | Thr | Asn | Ile | Gly 500 | Trp | Met | Val | Ser | Leu 505 | Arg | Tyr | Arg | Asn | Lys 510 | His |

| | | | | | | | | | | | | | | |
|---|---|---|---|---|---|---|---|---|---|---|---|---|---|---|
| Ile | Cys | Gly | Gly | Ser | Leu | Ile | Lys | Glu | Ser | Trp | Val | Leu | Thr | Ala | Arg |
| | | 515 | | | | | 520 | | | | | 525 | | | |
| Gln | Cys | Phe | Pro | Ser | Arg | Asp | Leu | Lys | Asp | Tyr | Glu | Ala | Trp | Leu | Gly |
| | | 530 | | | | 535 | | | | | 540 | | | | |
| Ile | His | Asp | Val | His | Gly | Arg | Gly | Asp | Glu | Lys | Cys | Lys | Gln | Val | Leu |
| 545 | | | | | 550 | | | | | 555 | | | | | 560 |
| Asn | Val | Ala | Gln | Leu | Val | Tyr | Gly | Pro | Glu | Gly | Ser | Asp | Leu | Val | Leu |
| | | | | 565 | | | | | 570 | | | | | 575 | |
| Met | Lys | Leu | Ala | Arg | Pro | Ala | Val | Leu | Asp | Asp | Phe | Val | Ser | Thr | Ile |
| | | | 580 | | | | | 585 | | | | | 590 | | |
| Asp | Leu | Pro | Asn | Tyr | Gly | Cys | Thr | Ile | Pro | Glu | Lys | Thr | Ser | Cys | Ser |
| | | 595 | | | | | 600 | | | | | 605 | | | |
| Val | Tyr | Gly | Trp | Gly | Tyr | Thr | Gly | Leu | Ile | Asn | Tyr | Asp | Gly | Leu | Leu |
| | 610 | | | | | 615 | | | | | 620 | | | | |
| Arg | Val | Ala | His | Leu | Tyr | Ile | Met | Gly | Asn | Glu | Lys | Cys | Ser | Gln | His |
| 625 | | | | | 630 | | | | | 635 | | | | | 640 |
| His | Arg | Gly | Lys | Val | Thr | Leu | Asn | Glu | Ser | Glu | Ile | Cys | Ala | Gly | Ala |
| | | | | 645 | | | | | 650 | | | | | 655 | |
| Glu | Lys | Ile | Gly | Ser | Gly | Pro | Cys | Glu | Gly | Asp | Tyr | Gly | Gly | Pro | Leu |
| | | | 660 | | | | | 665 | | | | | 670 | | |
| Val | Cys | Glu | Gln | His | Lys | Met | Arg | Met | Val | Leu | Gly | Val | Ile | Val | Pro |
| | | 675 | | | | | 680 | | | | | 685 | | | |
| Gly | Arg | Gly | Cys | Ala | Ile | Pro | Asn | Arg | Pro | Gly | Ile | Phe | Val | Arg | Val |
| | 690 | | | | | 695 | | | | | 700 | | | | |
| Ala | Tyr | Tyr | Ala | Lys | Trp | Ile | His | Lys | Ile | Ile | Leu | Thr | Tyr | Lys | Val |
| 705 | | | | | 710 | | | | | 715 | | | | | 720 |
| Pro | Gln | Ser | | | | | | | | | | | | | |

( 2 ) INFORMATION FOR SEQ ID NO:3:

( i ) SEQUENCE CHARACTERISTICS:
        ( A ) LENGTH: 723 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Trp | Val | Thr | Lys | Leu | Leu | Pro | Ala | Leu | Leu | Leu | Gln | His | Val | Leu |
| 1 | | | | 5 | | | | | 10 | | | | | 15 | |
| Leu | His | Leu | Leu | Leu | Leu | Pro | Ile | Ala | Ile | Pro | Tyr | Ala | Glu | Gly | Gln |
| | | | 20 | | | | | 25 | | | | | 30 | | |
| Arg | Lys | Arg | Arg | Asn | Thr | Ile | His | Glu | Phe | Lys | Lys | Ser | Ala | Lys | Thr |
| | | 35 | | | | | 40 | | | | | 45 | | | |
| Thr | Leu | Ile | Lys | Ile | Asp | Pro | Ala | Leu | Lys | Ile | Lys | Thr | Lys | Lys | Val |
| | 50 | | | | | 55 | | | | | 60 | | | | |
| Asn | Thr | Ala | Asp | Gln | Cys | Ala | Asn | Arg | Cys | Thr | Arg | Asn | Lys | Gly | Leu |
| 65 | | | | | 70 | | | | | 75 | | | | | 80 |
| Pro | Phe | Thr | Cys | Lys | Ala | Phe | Val | Phe | Asp | Lys | Ala | Arg | Lys | Gln | Cys |
| | | | | 85 | | | | | 90 | | | | | 95 | |
| Leu | Trp | Phe | Pro | Phe | Asn | Ser | Met | Ser | Ser | Gly | Val | Lys | Lys | Glu | Phe |
| | | | 100 | | | | | 105 | | | | | 110 | | |
| Gly | His | Glu | Phe | Asp | Leu | Tyr | Glu | Asn | Lys | Asp | Tyr | Ile | Arg | Asn | Cys |
| | | | | 115 | | | | | 120 | | | | | 125 | |
| Ile | Ile | Gly | Lys | Gly | Arg | Ser | Tyr | Lys | Gly | Thr | Val | Ser | Ile | Thr | Lys |
| | | | 130 | | | | | 135 | | | | | 140 | | |

| | | | | | | | | | | | | | | |
|---|---|---|---|---|---|---|---|---|---|---|---|---|---|---|
| Ser | Gly | Ile | Lys | Cys | Gln | Pro | Trp | Ser | Ser | Met | Ile | Pro | His | Glu | His |
| 145 | | | | | 150 | | | | | 155 | | | | | 160 |
| Ser | Tyr | Arg | Gly | Lys | Asp | Leu | Gln | Glu | Asn | Tyr | Cys | Arg | Asn | Pro | Arg |
| | | | | 165 | | | | 170 | | | | | 175 | | |
| Gly | Glu | Glu | Gly | Gly | Pro | Trp | Cys | Phe | Thr | Ser | Asn | Pro | Glu | Val | Arg |
| | | | 180 | | | | | 185 | | | | | 190 | | |
| Tyr | Glu | Val | Cys | Asp | Ile | Pro | Gln | Cys | Ser | Glu | Val | Glu | Cys | Met | Thr |
| | | 195 | | | | | 200 | | | | 205 | | | | |
| Cys | Asn | Gly | Glu | Ser | Tyr | Arg | Gly | Leu | Met | Asp | His | Thr | Glu | Ser | Gly |
| | 210 | | | | | 215 | | | | | 220 | | | | |
| Lys | Ile | Cys | Gln | Arg | Trp | Asp | His | Gln | Thr | Pro | His | Arg | His | Lys | Phe |
| 225 | | | | | 230 | | | | | 235 | | | | | 240 |
| Leu | Pro | Glu | Arg | Tyr | Pro | Asp | Lys | Gly | Phe | Asp | Asp | Asn | Tyr | Cys | Arg |
| | | | | 245 | | | | 250 | | | | | 255 | | |
| Asn | Pro | Asp | Gly | Gln | Pro | Arg | Pro | Trp | Cys | Tyr | Thr | Leu | Asp | Pro | His |
| | | | 260 | | | | | 265 | | | | | 270 | | |
| Thr | Arg | Trp | Glu | Tyr | Cys | Ala | Ile | Lys | Thr | Cys | Ala | Asp | Asn | Thr | Met |
| | | 275 | | | | | 280 | | | | 285 | | | | |
| Gln | Asp | Thr | Asp | Val | Pro | Leu | Glu | Thr | Thr | Glu | Cys | Ile | Gln | Gly | Gln |
| 290 | | | | | 295 | | | | | 300 | | | | | |
| Gly | Glu | Gly | Tyr | Arg | Gly | Thr | Val | Asn | Thr | Ile | Trp | Asn | Gly | Ile | Pro |
| 305 | | | | | 310 | | | | | 315 | | | | | 320 |
| Cys | Gln | Arg | Trp | Asp | Ser | Gln | Tyr | Pro | His | Glu | His | Asp | Met | Thr | Pro |
| | | | | 325 | | | | | 330 | | | | | 335 | |
| Glu | Asn | Phe | Lys | Cys | Lys | Asp | Leu | Arg | Glu | Asn | Tyr | Cys | Arg | Asn | Pro |
| | | | 340 | | | | | 345 | | | | | 350 | | |
| Asp | Gly | Ser | Glu | Ser | Pro | Trp | Cys | Phe | Thr | Thr | Asp | Pro | Asn | Ile | Arg |
| | | 355 | | | | | 360 | | | | | 365 | | | |
| Val | Gly | Tyr | Cys | Ser | Gln | Ile | Pro | Asn | Cys | Asp | Met | Ser | His | Gly | Gln |
| | 370 | | | | | 375 | | | | | 380 | | | | |
| Asp | Cys | Tyr | Arg | Gly | Asn | Gly | Lys | Asn | Tyr | Met | Gly | Asn | Leu | Ser | Gln |
| 385 | | | | | 390 | | | | | 395 | | | | | 400 |
| Thr | Arg | Ser | Gly | Leu | Thr | Cys | Ser | Met | Trp | Asp | Lys | Asn | Met | Glu | Asp |
| | | | | 405 | | | | | 410 | | | | | 415 | |
| Leu | His | Arg | His | Ile | Phe | Trp | Glu | Pro | Asp | Ala | Ser | Lys | Leu | Asn | Glu |
| | | | 420 | | | | | 425 | | | | | 430 | | |
| Asn | Tyr | Cys | Arg | Asn | Pro | Asp | Asp | Asp | Ala | His | Gly | Pro | Trp | Cys | Tyr |
| | | | 435 | | | | 440 | | | | | 445 | | | |
| Thr | Gly | Asn | Pro | Leu | Ile | Pro | Trp | Asp | Tyr | Cys | Pro | Ile | Ser | Arg | Cys |
| | 450 | | | | | 455 | | | | | 460 | | | | |
| Glu | Gly | Asp | Thr | Thr | Pro | Thr | Ile | Val | Asn | Leu | Asp | His | Pro | Val | Ile |
| 465 | | | | | 470 | | | | | 475 | | | | | 480 |
| Ser | Cys | Ala | Lys | Thr | Lys | Gln | Leu | Arg | Val | Val | Asn | Gly | Ile | Pro | Thr |
| | | | | 485 | | | | | 490 | | | | | 495 | |
| Arg | Thr | Asn | Ile | Gly | Trp | Met | Val | Ser | Leu | Arg | Tyr | Arg | Asn | Lys | His |
| | | | | 500 | | | | 505 | | | | | 510 | | |
| Ile | Cys | Gly | Gly | Ser | Leu | Ile | Lys | Glu | Ser | Trp | Val | Leu | Thr | Ala | Arg |
| | | 515 | | | | | 520 | | | | | 525 | | | |
| Gln | Cys | Phe | Pro | Ser | Arg | Asp | Leu | Lys | Asp | Tyr | Glu | Ala | Trp | Leu | Gly |
| | | 530 | | | | 535 | | | | | 540 | | | | |
| Ile | His | Asp | Val | His | Gly | Arg | Gly | Asp | Glu | Lys | Cys | Lys | Gln | Val | Leu |
| 545 | | | | | 550 | | | | | 555 | | | | | 560 |
| Asn | Val | Ala | Gln | Leu | Val | Tyr | Gly | Pro | Glu | Gly | Ser | Asp | Leu | Val | Leu |

|           |           |           |           |           |           | 565       |           |           |           |           | 570       |           |           |           |           | 575       |           |
|-----------|-----------|-----------|-----------|-----------|-----------|-----------|-----------|-----------|-----------|-----------|-----------|-----------|-----------|-----------|-----------|-----------|-----------|

Met Lys Leu Ala Arg Pro Ala Val Leu Asp Asp Phe Val Ser Thr Ile
                580                     585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610             615                 620

Arg Val Ala His Leu Tyr Ile Met Gly Asn Glu Lys Cys Ser Gln His
625             630                 635                         640

His Arg Gly Lys Val Thr Leu Asn Glu Ser Glu Ile Cys Ala Gly Ala
                645             650                 655

Glu Lys Ile Gly Ser Gly Pro Cys Glu Gly Asp Tyr Gly Gly Pro Leu
            660             665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695             700

Ala Tyr Tyr Ala Lys Trp Ile His Lys Ile Ile Leu Thr Tyr Lys Val
705             710                 715                     720

Pro Gln Ser (2) INFORMATION FOR SEQ ID NO:4:

(i) SEQUENCE CHARACTERISTICS:
        (A) LENGTH: 2288 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
TAGGCACTGA CTCCGAACAG GATTCTTTCA CCCAGGCATC TCCTCCAGAG GGATCCGCCA      60
GCCCGTCCAG CAGCACCATG TGGGTGACCA AACTCCTGCC AGCCCTGCTG CTGCAGCATG     120
TCCTCCTGCA TCTCCTCCTG CTCCCCATCG CCATCCCCTA TGCAGAGGGA CAAAGGAAAA     180
GAAGAAATAC AATTCATGAA TTCAAAAAAT CAGCAAAGAC TACCCTAATC AAAAAGATCC     240
AGCACTGAAG ATAAAAACCA AAAAGTGAA TACTGCAGAC CAATGTGCTA ATAGATGTAC      300
TAGGAATAAA GGACTTCCAT TCACTTGCAA GGCTTTTGTT TTTGATAAAG CAAGAAAACA     360
ATGCCTCTGG TTCCCCTTCA ATAGCATGTC AAGTGGAGTG AAAAAAGAAT TGGCCATGA      420
ATTTGACCTC TATGAAAACA AAGACTACAT TAGAAACTGC ATCATTGGTA AGGACGCAG      480
CTACAAGGGA ACAGTATCTA TCACTAAGAG TGGCATCAAA TGTCAGCCCT GGAGTTCCAT     540
GATACCACAC GAACACAGCT ATCGGGGTAA AGACCTACAG GAAAACTACT GTCGAAATCC     600
TCGAGGGGAA GAAGGGGGAC CCTGGTGTTT CACAAGCAAT CCAGAGGTAC GCTACGAAGT     660
CTGTGACATT CCTCAGTGTT CAGAAGTTGA ATGCATGACC TGCAATGGGG AGAGTTATCG     720
AGGTCTCATG GATCATACAG AATCAGGCAA GATTTGTCAG CGCTGGGATC ATCAGACACC     780
ACACCGGCAC AAATTCTTGC CTGAAAGATA TCCCGACAAG GGCTTTGATG ATAATTATTG     840
CCGCAATCCC GATGGCCAGC CGAGGCCATG GTGCTATACT CTTGACCCTC ACACCCGCTG     900
GGAGTACTGT GCAATTAAAA CATGCGCTGA CAATACTATG AATGACACTG ATGTTCCTTT     960
GGAAACAACT GAATGCATCC AAGGTCAAGG AGAAGGCTAC AGGGGCACTG TCAATACCAT    1020
TTGGAATGGA ATTCCATGTC AGCGTTGGGA TTCTCAGTAT CCTCACGAGC ATGACATGAC    1080
```

| | | | | | |
|---|---|---|---|---|---|
| TCCTGAAAAT | TTCAAGTGCA | AGGACCTACG | AGAAAATTAC | TGCCGAAATC | CAGATGGGTC | 1140 |
| TGAATCACCC | TGGTGTTTTA | CCACTGATCC | AAACATCCGA | GTTGGCTACT | GCTCCCAAAT | 1200 |
| TCCAAACTGT | GATATGTCAC | ATGGACAAGA | TTGTTATCGT | GGGAATGGCA | AAAATTATAT | 1260 |
| GGGCAACTTA | TCCCAAACAA | GATCTGGACT | AACATGTTCA | ATGTGGGACA | AGAACATGGA | 1320 |
| AGACTTACAT | CGTCATATCT | TCTGGGAACC | AGATGCAAGT | AAGCTGAATG | AGAATTACTG | 1380 |
| CCGAAATCCA | GATGATGATG | CTCATGGACC | CTGGTGCTAC | ACGGGAAATC | CACTCATTCC | 1440 |
| TTGGGATTAT | TGCCCTATTT | CTCGTTGTGA | AGGTGATACC | ACACCTACAA | TAGTCAATTT | 1500 |
| AGACCATCCC | GTAATATCTT | GTGCCAAAAC | GAAACAATTG | CGAGTTGTAA | ATGGGATTCC | 1560 |
| AACACGAACA | AACATAGGAT | GGATGGTTAG | TTTGAGATAC | AGAAATAAAC | ATATCTGCGG | 1620 |
| AGGATCATTG | ATAAAGGAGA | GTTGGGTTCT | TACTGCACGA | CAGTGTTTCC | CTTCTCGAGA | 1680 |
| CTTGAAAGAT | TATGAAGCTT | GGCTTGGAAT | TCATGATGTC | CACGGAAGAG | GAGATGAGAA | 1740 |
| ATGCAAACAG | GTTCTCAATG | TTTCCCAGCT | GGTATATGGC | CCTGAAGGAT | CAGATCTGGT | 1800 |
| TTTAATGAAG | CTTGCCAGGC | CTGCTGTCCT | GGATGATTTT | GTTAGTACGA | TTGATTTACC | 1860 |
| TAATTATGGA | TGCACAATTC | CTGAAAAGAC | CAGTTGCAGT | GTTTATGGCT | GGGGCTACAC | 1920 |
| TGGATTGATC | AACTATGATG | GCCTATTACG | AGTGGCACAT | CTCTATATAA | TGGGAAATGA | 1980 |
| GAAATGCAGC | CAGCATCATC | GAGGGAAGGT | GACTCTGAAT | GAGTCTGAAA | TATGTGCTGG | 2040 |
| GGCTGAAAAG | ATTGGATCAG | GACCATGTGA | GGGGGATTAT | GGTGGCCCAC | TTGTTTGTGA | 2100 |
| GCAACATAAA | ATGAGAATGG | TTCTTGGTGT | CATTGTTCCT | GGTCGTGGAT | GTGCCATTCC | 2160 |
| AAATCGTGCT | GGTATTTTTG | TCCGAGTCGC | ATATTATGCA | AAATGGATAC | ACAAAATTAT | 2220 |
| TTTAACATAT | AAGGTACCAC | AGTCATAGCT | GAAGTAAGTG | TGTCTGAAGC | ACCCACCAAT | 2280 |
| ACAACTGT | | | | | | 2288 |

( 2 ) INFORMATION FOR SEQ ID NO:5:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OLIGONUCLEOTIDE"

( x i ) SEQUENCE DESCRIPTION: SEQ ID NO:5:

TCAGTGTCCT GCATAGTAT                    19

( 2 ) INFORMATION FOR SEQ ID NO:6:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OLIGONUCLEOTIDE"

( x i ) SEQUENCE DESCRIPTION: SEQ ID NO:6:

CCAGATCTTG TTTGAGCTAA GTTGCCC               27

( 2 ) INFORMATION FOR SEQ ID NO:7:

( i ) SEQUENCE CHARACTERISTICS:
    ( A ) LENGTH: 21 base pairs
    ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:7:

GCTGGGATCA TCAGACACCA C              21

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:8:

ATACCAGCTG GGCAACATTG AGAAC              25

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:9:

GGCAACTTAT CCCAAACAAG ATCTGG              26

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:10:

ACTCTGAATG AGGCTGAAAT ATGTG              25

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:11:

GGCATGCACA GTTGTATTGG TGGGTGCTTC AG              32

( 2 ) INFORMATION FOR SEQ ID NO:12:

( i ) SEQUENCE CHARACTERISTICS:
        ( A ) LENGTH: 25 base pairs
        ( B ) TYPE: nucleic acid (C) STRANDEDNESS: single
(D) TOPOLOGY: linear (ii) MOLECULE TYPE: other nucleic acid
(A) DESCRIPTION: /desc = "OLIGONUCLEOTIDE"

(xi) SEQUENCE DESCRIPTION: SEQ ID NO:12:

CACATATTTC AGCCTCATTC AGAGT                        25

(2) INFORMATION FOR SEQ ID NO:13:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "OLIGONUCLEOTIDE"

(xi) SEQUENCE DESCRIPTION: SEQ ID NO:13:

AACAGGTTCT CAATGTTTCC CAG                          23

MODIFIED TUMOR CYTOTOXIC FACTOR (TCF) AND DNA ENCODING SUCH

FIELD OF THE INVENTION

This invention is related to genetically engineered modified TCFs which contain different number of N-linked oligosaccharide chains compared with wild type TCF, and have new amino-acid sequences. These modified TCFs obtained in this invention have longer serum half-lives, have growth stimulating activities for hepatocytes and cytotoxic activities against tumor cells. Therefore, the modified TCFs are useful as therapeutic agents against liver diseases and as anti-cancer drugs.

BACKGROUND OF THE INVENTION

TCF-II, tumor cytotoxic factor derived from human fibroblast, is a novel anti-tumor protein which is different from any other proteins so far reported. The inventors succeeded in cDNA cloning of this protein, deduced its entire amino-acid sequence and confirmed the usefulness. This novel anti-tumor protein and its cDNA were disclosed in W090/10651. They were designated as TCF-II. In this invention, the glycoprotein which has the amino-acid sequence disclosed in W090/10651 is called TCF. TCF is a substance which has been called TCF-II.

TCF has both strong cytotoxic activity against tumor cells and growth stimulating activity for normal cells. And it has been confirmed that TCF is member of a family including HGF, a growth factor for hepatocytes. The. molecular weight of TCF is 78000±2000 daltons and/or 74000±2000 daltons on SDS polyacrylamide gel electrophoresis. Under reducing conditions, it showed a polypeptide band called A chain with a molecular mass of 52000±2000 daltons and two polypeptide bands called B chain and/or C chain with molecular masses of 30000±2000 daltons and/or 26000±2000 daltons, respectively.

Because TCF is a growth factor for hepatocytes, application to liver regeneration after hepatectomy has been examined. Since biological half-life of TCF is very short, attempts have been made to obtain more effective modified TCFs with prolonged biological half-lives.

Relationship between oligosaccharide chains and serum half-lives has been investigated in some glycoproteins including erythropoietin. The investigations have demonstrated that glycoproteins with slightly different structure in oligosaccharide chains and with different biological activities can be synthesized from the same gene. It was known that glycosylated erythropoietin is different in the biological activities from non-glycosylated one. However, about the relationship between oligosaccharide chains and biological activities of TCF little was known.

DISCLOSURE OF THE INVENTION

The present inventors took notice of the usefulness of TCF, and investigated application of TCF to the treatment of tumors or liver diseases and utilization as diagnostic markers of diseases. TCF has a very short half-life of approximately 2 minutes. To obtain modified proteins with prolonged biological half-lives, the inventors constructed several genetically engineered TCFs with mutations in the polypeptide moiety and analyzed them. However, most of the modified proteins appeared to lose the biological activities. Then, to prolong the biological half-life without loss of the biological activity; the inventors paid attention to the four N-linked oligosaccharide chains attached to TCF and attempted to construct the new modified TCFs which have a deletion of one or more oligosaccharide chains.

The theme of this invention is to present the new modified TCFs which have different amino-acid sequences compared to the wild-type TCF, and decreased number of N-linked oligosaccharide chains and longer biological half-lives than the wild-type TCF. These modified TCFs can be obtained by altering the nucleotide sequence of TCF cDNA encoding the amino acid residues responsible for N-glycosylation and by expressing the genetically mutagenized TCF cDNAs. Modified TCFs presented by the invention have one or more deletion(s) of the four N-linked oligosaccharide chains present in the wild-type TCF. These are the first modified TCFs with prolonged biological half lives without any loss of the biological activities, obtained by altering the amino-acid residues of the wild-type TCF.

FIG. 1 shows the entire amino-acid sequence of the wild-type TCF deduced from its cDNA sequence (Seq. Id No. 1). Amino-acid residues responsible for N-glycosylation are underlined. It is speculated that the signal sequence is removed and the glutamine residue at position 32nd results in the N-terminal amino acid of TCF. Four N-linked oligosaccharide chains bind to asparagine residues at positions 258th, 366th, 530th, and 617th relative to the N-terminal amino acid. These asparagine residues correspond to those at positions 89th, 397th, 561st, and 648th in FIG. 1.

FIG. 2 shows cDNA sequence (Seq. Id No. 4) encoding the amino-acid sequence. The coding region starts at the ATG codon marked with a circle in the figure.

Amino-acid residues responsible for N-glycosylation are Asn-X-Thr or Asn-X-Ser (amino-acid residues are indicated by the three-letter code and the X represents any amino-acid residues). Modified TCF lacking specific oligosaccharide chain(s) can be obtained by expressing the nucleotide sequence in which the codons for Asn, Ser or Thr are deleted or substituted with those for one of the other amino acids, in eukaryotic cells, preferably mammalian cells. Modified TCF which lacks specific oligosaccharide chains can be obtained by replacing the codons for Asn with those for other amino acids such as Gln, a substitution with little effects on the conformation of TCF. Gln is the most preferable amino acid which substitutes for Asn. Asp, Glu, His, Ser or Thr are also acceptable. Modified TCF lacking specific oligosaccharide chain(s) can be obtained by replacing the codons for Ser with those for other amino acids such as Ala, a substitution with little effects on the conformation of TCF. Ala is the most preferable amino acid which substitute for Ser. Pro, Gly or Asn are also acceptable. Modified TCF lacking specific oligosaccharide chain(s) can be obtained by deleting or replacing the codons for Thr to other amino acids. Ala is the most preferable amino acid which substitutes for Thr. Val, His or Asn ark also acceptable.

N-glycosylation sites are indicated in a schematic structure of TCF in FIG. 3. The N-glycosylation sites are designated as numbers 1, 2, 3 and 4 from N-terminal. These numbers specify the positions of the N-glycosylation sites.

To alter the amino-acid sequences responsible for N-glycosylation into those for non-glycosylation, the cDNA can be site-specifically mutagenized by PCR(polymerase chain reaction). The reactions are performed by cDNA for the wild-type TCF as the template and synthetic oligonucleotides as the primers. The sequences of primers are designed to delete or substitute the DNA sequences as described above. Other methods for mutagenesis are also applicable.

The cell lines producing the modified TCFs can be established by transforming host cells with expression vectors containing these mutant cDNAs. The modified TCFs can be recovered from the cultured broth of the transformed cell lines.

For example, to substitute Asn at position 289th (FIG. 1), binding site for oligosaccharide chain 1, cDNA was mutagenized by in vitro mutagenesis or mutagenesis by PCR. These mutagenesis reactions are performed by cDNA coding the wild-type TCF disclosed in WO 90/10651 as the template and synthetic oligonucleotide TCF-1R 5'-TCAGTGTCCTGCATAGTAT-3' (Seq. Id No. 5) as the primer. An expression vector containing the mutagenized cDNA can be transferred into eukaryotic cell lines including mammalian cell lines. The modified TCFs can be recovered from the cultured supernatants of the transfected cells.

Any types of host-vector systems for eukaryotic cells are acceptable for expression of the modified TCFs. The most preferable is a combination of cytomegalovirus promoter and Namalwa cells, which was disclosed in WO 92/1053. Commonly used systems including a gene amplification system using a combination of SV 40 promoter, DHFR gene and CHO cell line or an expression system using a combination of the replication origin of bovine papiloma virus and mouse C127 cell line can be enumerated.

Any commonly used methods for purification of biologically active proteins, can be used for purification of the modified TCFs, for example, precipitation by organic solvent, salting out, gel exclusion chromatography, affinity chromatography using monoclonal antibody or electrophoresis. Monoclonal antibodies against the wild-type TCF disclosed in Japanese Patent application number, 3-177236 can be used for affinity chromatography of modified TCF.

The modified TCFs can be stored lyophilized or frozen.

Fifteen modified TCFs can be obtained by combinations of the removal of the oligosaccharide chains. The modified TCFs are identified by numbers removed oligosaccharide chains. For example, the modified TCF which lacks oligosaccharide chain 1 is named TCF-1, the modified TCF which lacks all four oligosaccharide chains is named TCF-1234, and the modified TCF which lacks oligosaccharide chains 2 and 3 is named TCF-23. FIG. 4 schematically represents the N-linked oligosaccharides bound to the modified TCF. All the modified TCFs have different molecular masses according to the removal of oligosaccharide chains.

BRIEF DESCRIPTION OF THE DRAWINGS

FIG. 1 shows the entire amino-acid sequence of the wild-type TCF deduced from its cDNA sequence. Amino-acid residues responsible for binding of N-linked oligosaccharide chains are underlined.

FIG. 2 shows the cDNA sequence for the wild-type TCF. Codons to be substituted in the present invention are underlined. The coding sequence starts at the ATG codon marked with a circle.

(1) TCF, TCF-1, TCF-2, TCF-3 and TCF-4

(2) TCF-12, TCF-13, TCF-14, TCF-23, TCF-24 and TCF-34

(3) TCF-123, TCF-124, TCF-1234, TCF-134 and TCF-234

Figure 9:
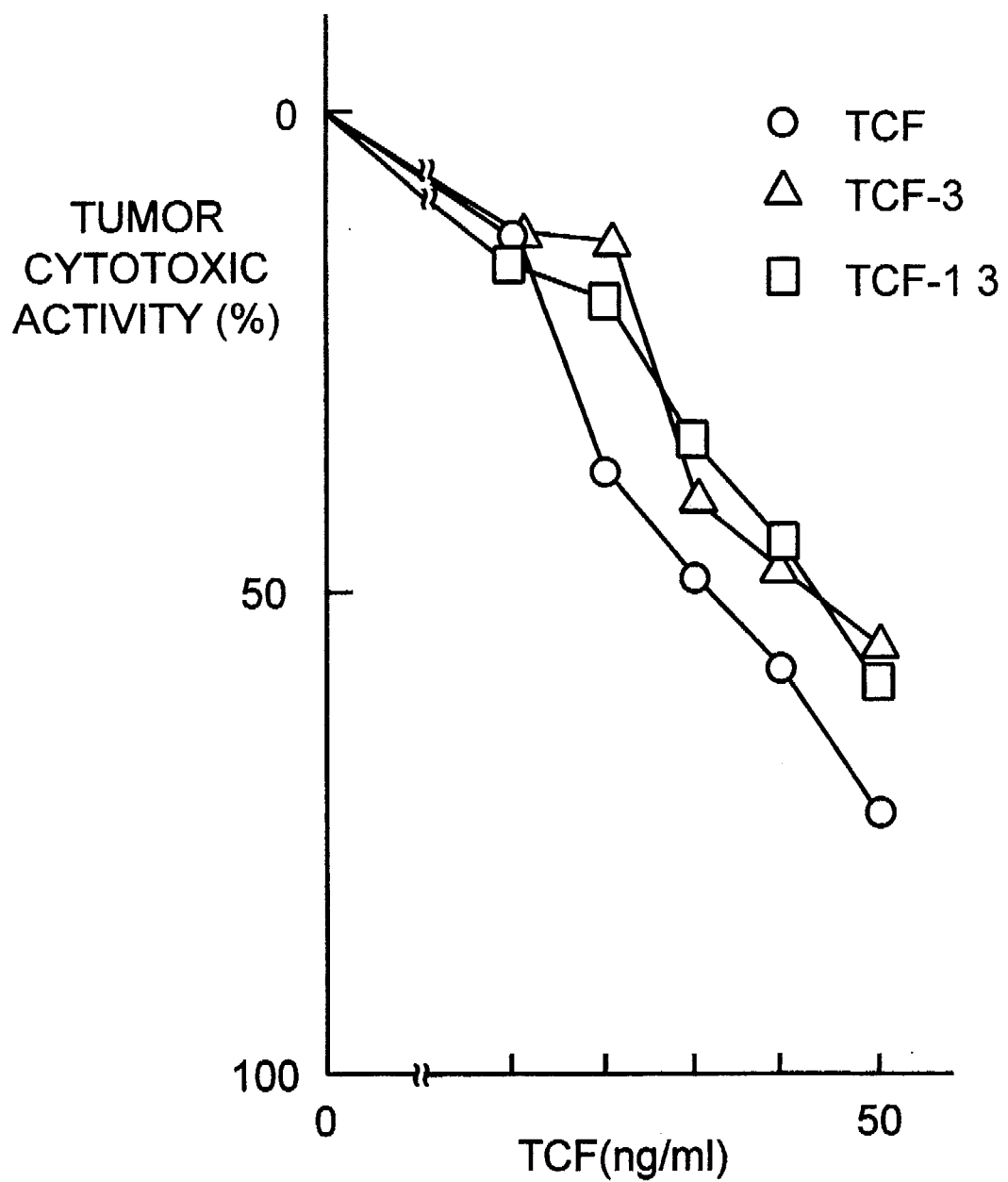

FIG. 9 shows the tumor cytotoxic activities of the modified TCF.

Figure 10:
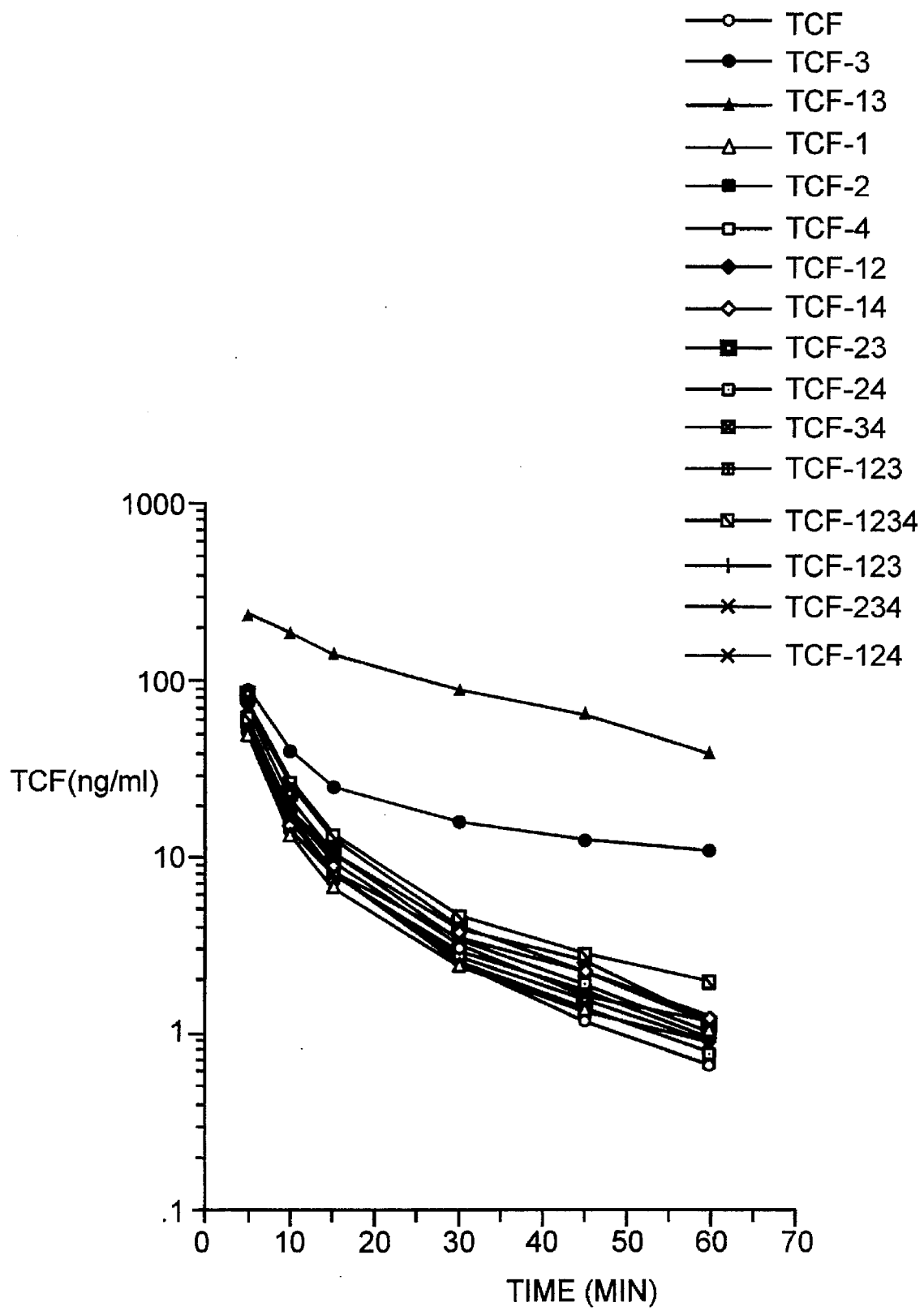

FIG. 10 shows the plasma concentrations of the modified TCF in the rats into which said modified TCFs were intravenously injected.

The novel modified TCFs are obtained by operating the present inventions. The modified TCFs obtained by the present invention can be prepared by expressing the cDNAs in which the codons for the amino-acid residues; responsible for N-glycosylation are substituted with those for other amino acids or are deleted. The modified TCFs have longer biological half-lives due to the control of the numbers and the binding sites of the N-linked oligosaccharide chains.

BEST MODE FOR PRACTICE OF THE INVENTION

In the examples herein, the present invention is described in more detail.

EXAMPLE 1

Preparation of the modified TCFs.

DNAs were manipulated essentially as described in Molecular Cloning, A Laboratory Manual, Second Edition, J. Sambrook, E. F. Fritsch, T. Maniatis, Cold Spring Habor Laboratory Press, New York, 1989 to prepare modified TCFs as described below.

① Cloning of TCF cDNA.

Site-specific mutations were introduced into TCF cDNA as described below by a 6.3-kb TCF expression plasmid, pcDTCF II, prepared by the method disclosed in WO92/01053. The E. coli strain containing pcDTCF II has been deposited to National Institute of Bioscience and Human-Technology as FERM BP-3479.

② Methods for introducing site-specific mutations.

1) Method 1 i) Cloning of TCF cDNA into M13mp18.

The plasmid pcDTCFII (6.3 kb) was prepared by introducing the entire coding region of human TCF cDNA into plasmid pcDNA I (Invitrogen Co.) digested with restriction enzymes BamHI and SphI (Takara Co.). (/All the restriction enzymes and the modifying enzymes were purchased from Takara Co.) pcDTCFII was digested with BamHI and SphI for 1 hour at 37° C., precipitated with ethanol, and electrophoresed on 1% agarose gel. The 2.3 kb of TCF cDNA fragment was purified from the gel by Gene Clean (Bio101 Co.).

On the other hand, replicative-form of phage DNA, M13mp18 (Takara Co.) as digested with BamHI and SphI, precipitated with ethanol, and dissolved in water to make the vector DNA solution. The vector DNA solution and TCF cDNA were mixed and ligated by the DNA Ligation Kit (Takara Co.). A part of the ligation mixture was used for transformation of E. coli, DH5α. The transformants were mixed with E. coli, NM522, an indicator strain, (Invitrogen Co.) and poured onto the LB soft agar plates containing 1% of bacto-tryptone, 0.5% of bacto-yeast extract, 1% of sodium chloride, 1% of IPTG (isopropyl-β-D-thiogalactoside, Takara Co.), and 1% of Xgal (5-bromo-4-chloro-3-indolyl-β-D-galactoside, Takara Co.) in order to make plaques. The double-stranded phage DNA was prepared from a clear plaque and the single-stranded DNA was prepared and used as a template for introducing site-specific mutations.

ii) Introduction of site-specific mutation.

The codon for the 289th amino acid,/Asn, in a consensus amino acid sequence for N-glycosylation, Asn-X-Thr, was replaced with a codon for Gln that does not make the consensus amino-acid sequence for N-glycosylation.

The definition of the number of amino acid is based on Met at the N-terminal of the wild-type as the first amino acid. The oligonucleotide TCF-1R, 5'-TCAGTGTCCTGCATAGTAT-3' (SEQ ID NO. 5), was synthesized by a DNA synthesizer (Applied Biosystems Co.). All the oligonucleotides were synthesized by the synthesizer unless otherwise noted.

Introduction of site-specific mutation was carried out by the oligonucleotide-directed in vitro mutagenesis system (Amersham Co.) according to the manufacture's instruction. *E. coli*, NH522 was transformed with the reaction mixture and screened with TCF-1 primer by the plaque hybridization technique.

The single-stranded DNA was prepared from a positive plaque and the sequence was determined by the dideoxy chain termination method described by Sanger et al. to confirm that the codon, AAT, for Asn at 289th, was replaced with the codon, CAG, for Gln. The 1.4-kb PstI-HindIII DNA fragment was prepared from the double-stranded DNA from the positive clone, ligated to PstI-HindIII-digested pBluescript SK+ (Stratagene Co.) to produce plasmid, pSKTCFPH-1.

2) Method 2

Introduction of site-specific mutations in the codons for the 399th, 563rd, and 650th amino acids were carried out essentially as described by R. Higuchi (R. Higuchi, PCR protocols, p.177–183, Academic Press, 1990) using polymerase chain reaction (PCR).A codon for Ser in a consensus amino acid sequence for N-glycosylation, Asn-X-Ser, was replaced with a codon for Ala in each mutagenesis.

To mutagenize the codon for Ser at 399th, 25 cycles of PCR were carried out by a mutant primer, TCF-2R 5'-CCAGATCTTGTTTGAGCTAAGTTGCCC-3' (SEQ ID NO. 6), a wild type primer, TCF701F 5'-GCTGGGATCATCAGACACCAC-3' (SEQ ID NO. 7), AmpliTaq polymerase (Takara Co.), and 4 ng of the plasmid pcDTCF II as a template. The PCR products were purified by centricon 100 (Amicon Co.) to remove primers, digested with restriction enzymes, BglII and EcoRI (Takara Co.), and ligated to the 4.1 kb DNA fragment of BglII-EcoRI-digested pSKTCFPH, plasmid previously produced by ligating PstI-HindIII-digested pBluescript SK+ and 1.4 kb fragment of the PstI-HindIII-digested pcDTCF II. A part of the ligation mixture was used for transformation of *E. coli*, DH5α. The plasmid DNAs were prepared from ampicillin resistant transformants and the DNA sequences were determined to screen for plasmid pSKTCFPH-2 in which the codon, TCC, for Ser at 399th was replaced with the codon, GCT, for Ala. Plasmid pSKTCFPH-12 was produced by ligating PCR products and the 4.1 kb DNA fragment of the BglII-EcoRI digested plasmid, pSKTCFPII-1 in a similar way. The DNA sequences of the portion of DNAs derived from PCR products in all plasmids were determined to confirm their sequences. Ampicillin was purchased from Sigma Co.

To mutagenize the codon for Ser at 563rd, 25 cycles of PCR were carried out by a mutant primer, TCF-3R 5'-ATACCAGCTGGGCAACATTGAGAAC-3' (Seq Id No. 8), a wild type primer, TCF1202F 5'-GGCAACTTATCCCAAACAAGATCTGG-3' (SEQ ID NO. 9), AmpliTaq polymerase (Takara Co.), and 4 ng of the plasmid pcDTCF II as a template. The PCR products were purified by centricon 100 (Amicon Co.) to remove primers, digested with restriction enzymes, XhoI and PvuII (Takara Co.). pcDTCF II was digested with XhoI and ligated to generate pcDTCF ΔXho, which lacks the 1.1 kb XhoI DNA fragment. pcDTCF ΔXho was digested with SphI and PvuII and the 4.8 kb of XhoI-SphI DNA fragment and the 0.5 kb of PvuII-SphI fragment were purified and ligated to XhoI-PvuII-digested PCR products described above by the DNA Ligation Kit. A part of the ligation mixture was used for transformation of *E. coli*, MC1061/P3 (Invitrogen Co.).

The plasmid DNAs were prepared from ampicillin- and tetracycline-resistant transformants and plasmid, pcDTCF ΔXhoI-3 in which the codon, TCC, for Ser at 563rd was replaced with the codon, GCC, for Ala, was selected in a similar way. Tetracycline was purchased from Sigma Co.

Two rounds of PCR were carried out to mutagenize the codon for Ser at 650th. The first PCRs were carried out independently by AmpliTaq polymerase (Takara Co.), 4 ng of the plasmid pcDTCF II as a template, and a pair of a mutant primer, TCF-4F 5'-ACTCTGAATGAGGCTGAAATATGTG-3' (SEQ ID NO. 10) and a wild type primer, TCF2203R 5'-GGCATGCACAGTTGTATTGGTGGGTGCTTCAG-3' (SEQ ID NO. 11) or a pair of a mutant primer, TCF-4R 5'-CACATATTTCAGCCTCATTCAGAGT-3' (SEQ ID NO. 12) and a wild type primer, TCF1685F 5'-AACAGGTTCTCAATGTTTCCCAG-3'. The PCR products were purified by DE81 paper (Whattman Co.) and one tenth of them was used for the second PCR by the primers, TCF2203R and TCF1685F. The PCR product was separated in an agarose gel, purified by DE81 paper and digested with BglII and SphI. On the other hand, pcDTCFΔXhoI and pcDTCF ΔXhoI-3 were digested with BglII and SphI and the 4.9 kb of DNA fragments were purified, ligated to the BglII-SphI-digested PCR fragment described above by the DNA Ligation Kit. One tenth of the ligation mixtures was used to transform *E. coli*, MC1061/P3. The plasmid DNA were prepared from ampicillin- and tetracycline-resistant transformants and plasmid, pcDTCFΔXhoI-4 in which the codon, TCT, for Ser at 650th, was replaced with the codon, GCT, for Ala and plasmid, pcDTCF ΔXhoI-34 in which both codons for Ser at 563rd and at 650th were replaced with the codons for Ala, were selected, in a similar way.

③ Construction of expression vectors.

1) Construction of vectors for transient expression.

Figure 3:
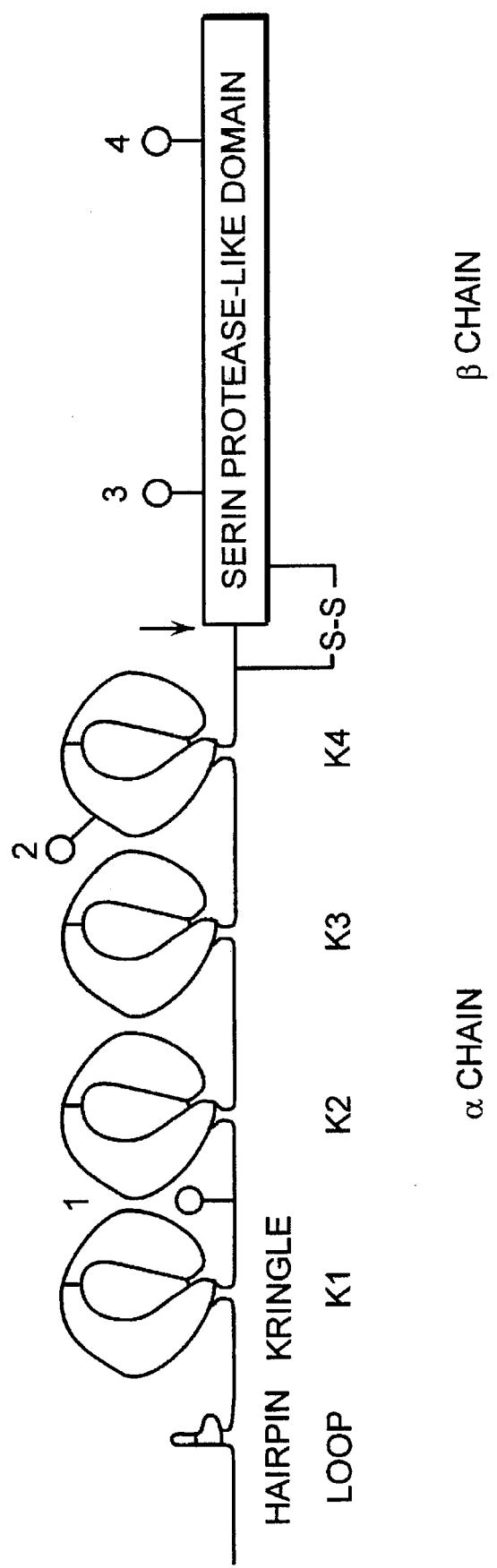
FIG. 3 schematically represents the primary structure of the wild-type TCF. Circles represent the N-glycosylation sites and the arrow shows the cleavage site between A chain and B chain.
Figure 4:
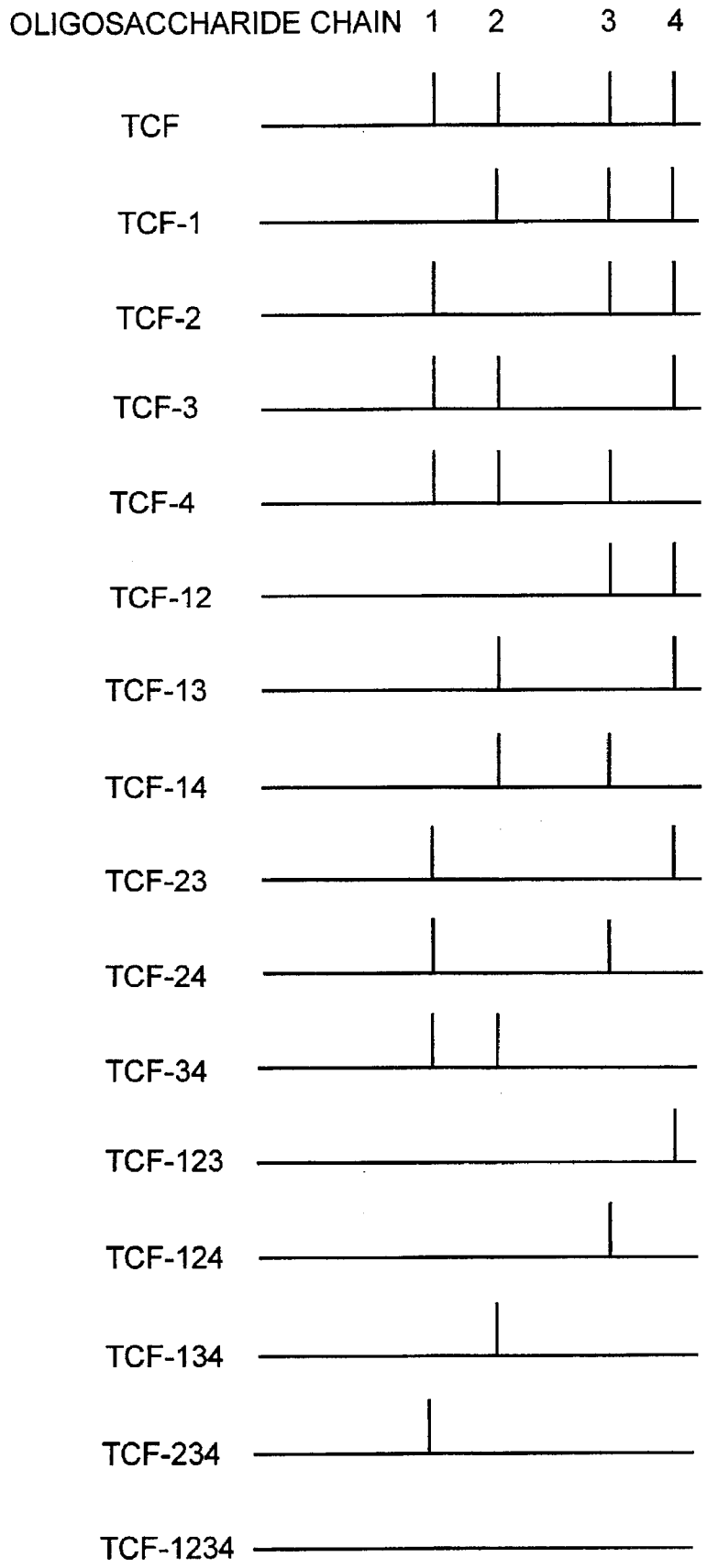
FIG. 4 schematically represents the oligosaccharide chains attached to TCF and the modified TCF. The horizontal lines represent the polypeptides and the vertical bars represents the oligosaccharide chains.
Figure 5:
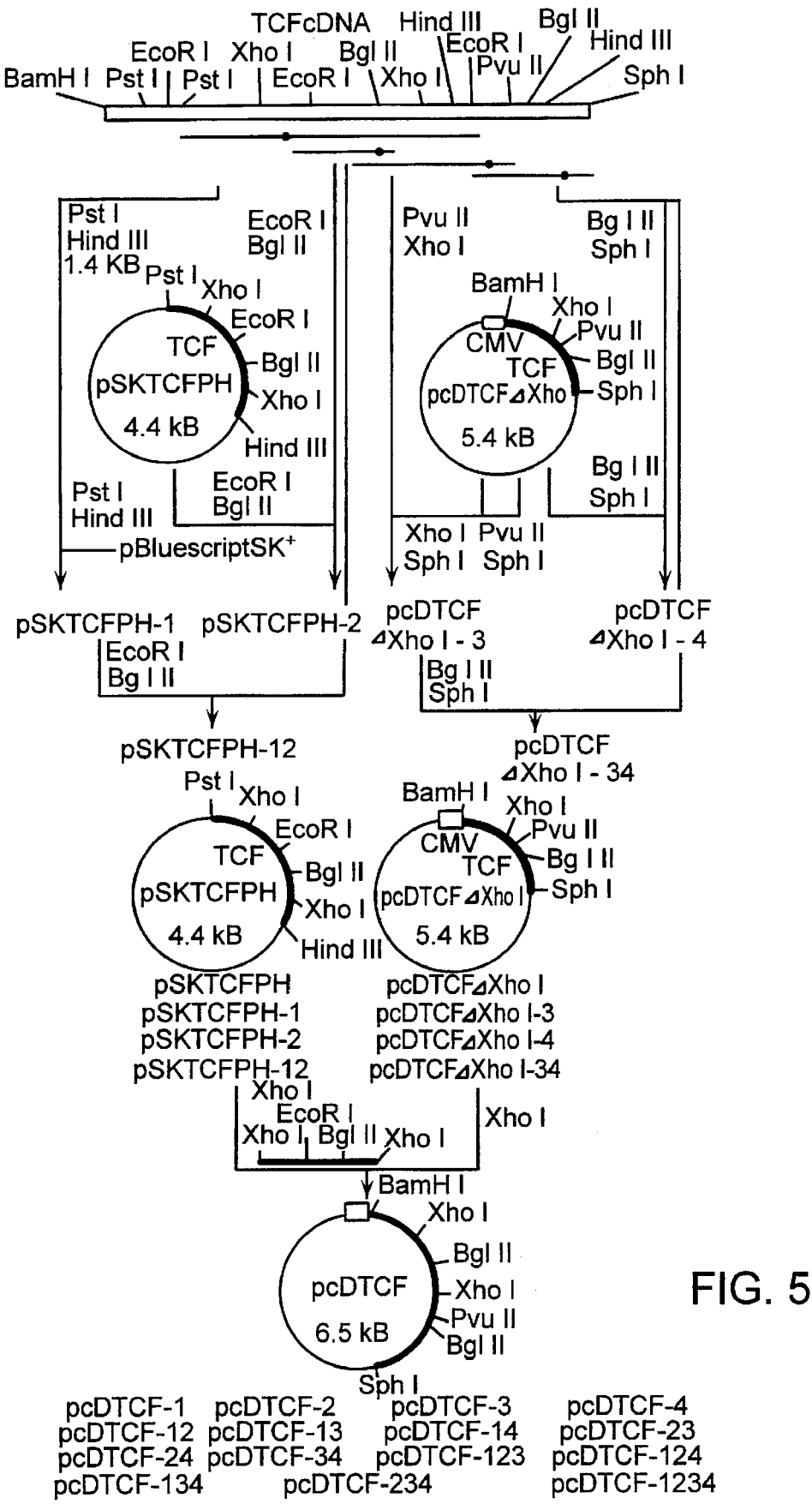
FIG. 5 shows the construction of the plasmids containing cDNAs for the modified TCF.
Figure 6:
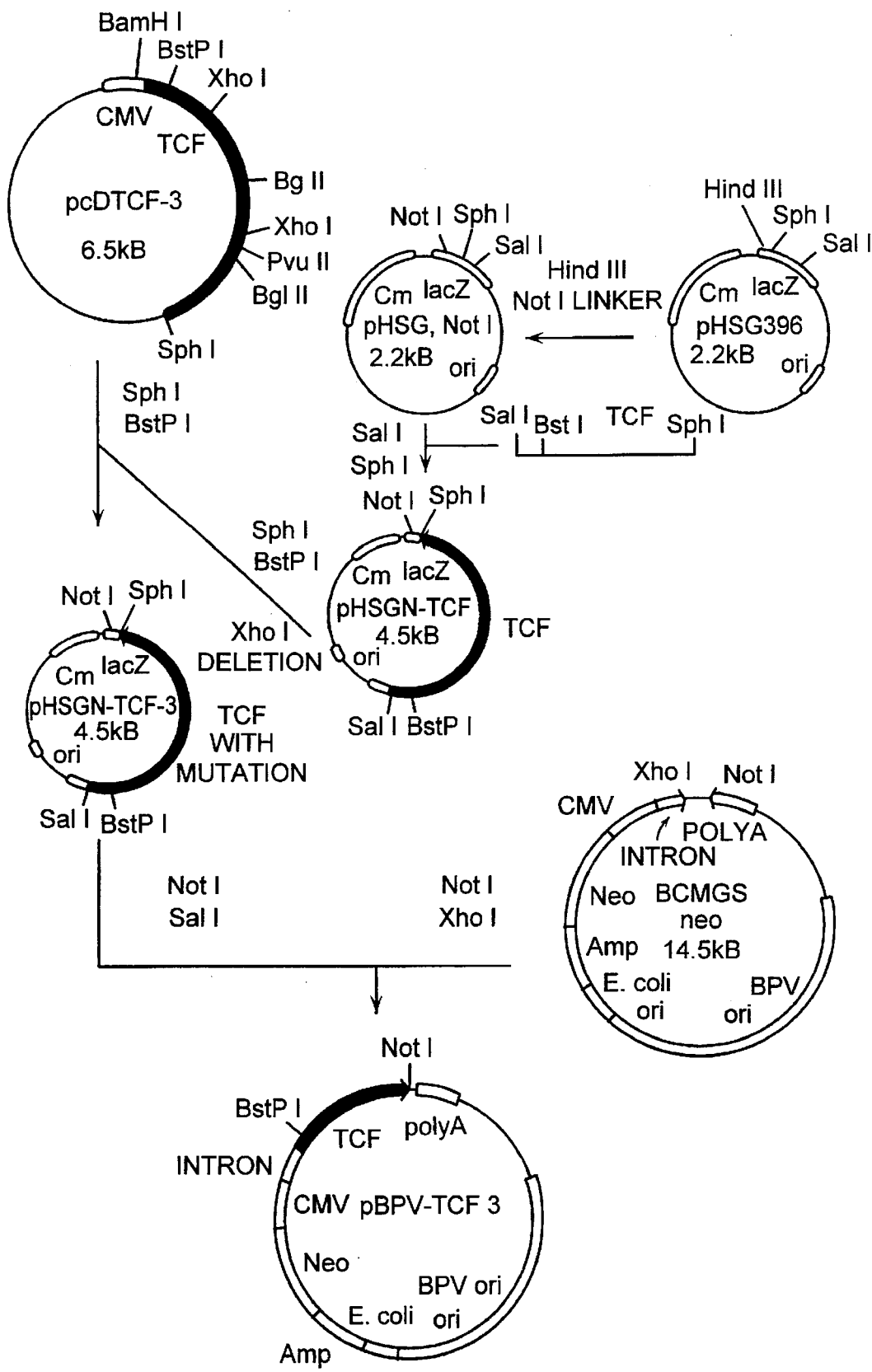
FIG. 6 shows the construction of the expression vectors for TCF and the modified TCF.

Plasmids, pSKTCFPH, pSKTCFPH-1, pSKTCFPH-2, and pSKTCFPH-12were digested with XhoI and 1.1 kb of DNA fragments were purified. Plasmids, pcDTCF ΔXhoI, pcDTCFΔXhoI-3, pcDTCFΔXhoI-4, and pcDTCFΔXhoI-34 were digested with XhoI and ligated to four kinds of 1.1 kb of DNA fragments described above. Fifteen ligation mixtures except the combination of 1.1 kb of pSKTCFPH and pcDTCF ΔXhoI were used to transform *E. coli*, MC1061/P3. Fifteen expression vectors, pcDTCF-1, pcDTCF-2, pcDTCF-3, pcDTCF-4, pcDTCF-12, pcDTCF-13, pcDTCF-14, pcDTCF-23, pcDTCF-24, pcDTCF-34, pcDTCF-123, pcDTCF-124, pcDTCF-134, pcDTCF-234, and pcDTCF-1234were selected. Analysis by restriction enzymes has confirmed the structures of these vectors. When these plasmids are transfected into mammalian cells, for instance COS cells, genes for TCF and the modified TCF are expressed under the control of cytomegalovirus (CMV) promoter. The construction of these plasmids are shown in FIG. 5.

2) Construction of vectors for stable expression.

Plasmid pHSG396 (Takara Co.) was digested with HindIII, blunt-ended with the DNA Blunting Kit (Takara Co.), purified with Gene Clean, ligated to NotI linker, 8 mer 5'-GCGGCCGC-3' (Takara Co.), and used to transform *E. coli*, DH5α. The plasmid DNAs were prepared from chloramphenicol resistant transformants and plasmid, pHSG NotI, which did not contain HindIII site but contain NotI site was selected. pHSG NotI, was digested with SalI and SphI and ligated to the 2.3 kb of full-length TCF cDNA digested with SalI and SphI to produce plasmid, pHSG N-TCF. The 1.1 kb of XhoI-XhoI fragment was deleted from the plasmid, pHSG N-TCF, to produce plasmid, pHSG N-TCFII ΔX. pHSG N-TCFII ΔX, was digested with BstPI and SphI and the 2.3 kb of DNA fragment was purified, ligated to the BstPI-SphI-digested 15 plasmids, pcDTCF-1, pcDTCF-2, pcDTCF-3, pcDTCF-4, pcDTCF-12, pcDTCF-13, pcDTCF-14, pcDTCF-23, pcDTCF-24, pcDTCF-34, pcDTCF-123, pcDTCF-124, pcDTCF-134, pcDTCF-234, and pcDTCF-1234, and the BstPI-SphI-digested pcDTCF that contained the wild type TCF cDNA by DNA Ligation Kit, and used to transform *E. coli*, DH5α. The plasmid DNAs were prepared from chloramphenicol-resistant transformants and the 16 plasmids that contained 2.3 kb of the wild-type TCF or each of the mutant TCF cDNAs in the plasmid, pHSG NotI, were selected.

These plasmids were designated as pHSGN-TCF, pHSGN-TCF-1, pHSGN-TCF-2, pHSGN-TCF-3, pHSGN-TCF-4, pHSGN-TCF-12, pHSGN-TCF-13, pHSGN-TCF-14, pHSGN-TCF-23, pHSGN-TCF-24, pHSGN-TCF-34, pHSGN-TCF-123, pHSGN-TCF-124, pHSGN-TCF-134, pHSGN-TCF-234, and pHSGN-TCF-1234. These 16 plasmids were digested with SalI and NotI, ligated to the XhoI-NotI-digested expression vector, BCHGSneo, and used to transform *E. coli*, DH5α. BCHGSneo is a plasmid that contains the replication origin of bovine papiloma virus and cytomegalovirus promoter, and is capable of replicating in *E. coli*. BCHGSneo is provided by Dr. H. Karasuyama in Basel Immunology Institute and is described in Idenshikohgaku hand book, p297–299, Yohdo Co., 1991. The plasmid DNAs were prepared from ampicillin resistant transformants and the 16 expression vectors that contained 2.3 kb of wild-type TCF or each of the mutant TCF cDNAs in BCHGSneo were selected. These plasmids were designated as, pBPV-TCF, pBPV-TCF-1, pBPV-TCF-2, pBPV-TCF-3, pBPV-TCF-4, pBPV-TCF-12, pBPV-TCF-13, pBPV-TCF-14, pBPV-TCF-23, pBPV-TCF-24, pBPV-TCF-34, pBPV-TCF-123, pBPV-TCF-124, pBPV-TCF-134, pBPV-TCF-234, and pBPV-TCF-1234. Antibiotics, chloramphenicol was purchased from Sigma Co. *E. coli* strains containing pBPV-TCF-3 or pBPV-TCF-13 were deposited to National Institute of Bioscience and Human Technology as FERM BP-4454 and FERM BP-4455.

④ Preparation and purification of the TCF or the modified TCFs expression plasmids.

The 16 *E. coli* strains containing each of the expression vectors, pBPV-TCF, pBPV-TCF-1, pBPV-TCF-2, pBPV-TCF-3, pBPV-TCF-4, pBPV-TCF-12, pBPV-TCF-13, pBPV-TCF-14, pBPV-TCF-23, pBPV-TCF-24, pBPV-TCF-34, pBPV-TCF-123, pBPV-TCF-124, pBPV-TCF-134, pBPV-TCF-234, and pBPV-TCF-1234, were cultured in 400 ml of medium containing 50 µg/ml of ampicillin at 37° C. When the absorbance at 600 nm of each culture broth reached 0.8, chloramphenicol was added to the broth at a final concentration of 170 µg/ml and each broth was cultured overnight. These 16 plasmids were prepared by the alkali-SDS method and purified by cesium chloride density gradient ultra centrifugation as described by Maniatis et. al. (Molecular Cloning 2nd ed.).

⑤ Transfection of the TCF- and the modified TCF- expression plasmids into the cultured animal cell lines.

The 16 expression plasmids were transfected into a mouse cell line, C 127 by TRANSFECTM (IBF Co. Maryland, USA), DNA transfection reagent for cultured mammalian cell lines, as described below. One day prior to transfection, approximately $10^6$ cells of mouse C127 were suspended in DME medium (GIBCO Co.) containing 10% of fetal calf serum and incubated at 37° C. overnight in a $CO_2$ incubator (a humidified incubator in an atmosphere of 5–7% of $CO_2$), in 25 cm$^2$ tissue culture flasks (Sumitomo Bakelite, for adherent cells). (Cells were cultured at 37° C. in a humidified incubator in an atmosphere of 5–7% $CO_2$, unless otherwise noted.). The cells were washed twice with Opti. MEM medium (GIBCO Co.) before transfection. After adding 2 ml of Opti. MEM to the monolayer of the cells, transfection was carried out by 10 µg of the plasmid DNA as described in the manufacturer's protocol. After incubated for 6 hours, 7.5 ml of DME medium was added to the flasks. Then, the cells were incubated for two more days at 37° C. The medium was replaced with fresh DME medium on the first day. The cells were trypsinized, washed once with DME medium and suspended in 50 mL of DME medium containing 100 µg/ml of G418. One hundred micro-liter of the suspension was added to each well in a 96-well flat-bottomed plates and incubated at 37° C. One week later, 100 µL of DME medium containing 100 µg/ml of G418 was added to each well, and the plates were incubated at 37° C. Another week later, expression of the TCF or the modified TCFs was detected by measuring the concentration of TCF or the modified TCFs in 100 µL of the cultured media by an enzyme immuno assay employing anti-TCF monoclonal antibodies (N. Shima et. al. Gastroenterologia Japonica 26 (4) 477–482, 1991). The cell lines expressing TCF or the modified TCFs were cultured at 37° C. in a 12-well tissue culture plate or in a 25 cm$^2$ flask according to the cell numbers. Cell lines which express the modified TCFs (a total of 15 modified TCFs designated as TCF-1, TCF-2, TCF-3, TCF-4, TCF-12, TCF-13, TCF-14, TCF-23, TCF-24, TCF-34, TCF-123, TCF-124, TCF-134, TCF-234, and TCF-1234) were thus obtained.

⑥ Large-scale cultivation of the cell lines which produce TCF or the modified TCFs.

The confluent cells producing TCF or the modified TCFs in 75 cm$^2$ tissue culture flasks were harvested by trypsinization, followed by inoculating into three 225 cm$^2$ tissue culture flasks. One hundred milliliters of DME medium was added to each flask and the culture was incubated at 37° C. Four days later, the confluent cells were trypsinized and suspended in the DME medium. The cell suspension was diluted 10-fold with DME medium (a total volume of 3 L). One hundred milliliters of the diluted cell suspension was inoculated into a new 225 cm$^2$ tissue culture flask. The cells were cultured at 37° C. for 5 days in thirty 225 cm$^2$ tissue culture flasks. The cultured supernatant (a total volume of 3 L) was collected. Cells were harvested from 6 flasks, followed by inoculating into sixty 225 cm$^2$ tissue culture flasks. To each flask, 100 ml of the medium was added and incubated at 37° C. for 5 days. The cultured supernatant (a total volume of 6 L) was collected. Thus, 9 L of the cultured supernatant which contains the TCF or the modified TCFs was obtained.

⑦ Purification of the TCF and the modified TCFs.

A three-step purification was performed as described below.

1) Heparin-sepharose CL-6B

Nine liters of the cultured supernatant which contains each of the modified TCF was centrifuged at 6,000 rpm for 30 min. to remove insoluble materials. The supernatant was applied at an approximate flow rate of 200 ml per hour to a heparin-sepharose CL-6B column (2.5×12 cm) (Pharmacia Co.) which had been equilibrated with 300 mL of the equilibration buffer,10 mM Tris-HCl buffer (pH 7.5) containing 0.5M of NaCl and 0.01% of Tween 20. The column was then washed with approximately 700 mL of the equilibration buffer. The TCF or the modified TCFs were eluted with 10 mM Tris-HCl buffer (pH 7.5) containing 2M NaCl and 0.01% of Tween 20 and the fractions of 3 mL were collected. The fractions were monitored by the absorbance at 280 nm and the fractions containing TCF or the modified TCFs (approximately 100 mL) were obtained.

2l) Mono S-FPLC

The eluate which contains TCF or the modified TCFs was dialyzed against 10 mM of phosphate buffer (pH 6.5) containing 0.15M of NaCl and centrifuged at 12,000 rpm for 90 min. to remove insoluble materials. The supernatant was applied at a flow rate of 1 mL/min. to a Mono S column (0.5×5 cm, Pharmacia, FPLC) which had been equilibrated with approximately 20 ml of 10 mM phosphate buffer (pH 7.0) containing 0.15M NaCl and 0.01% Tween 20 (buffer A). The column was washed once with approximately 30 mL of buffer A. Then the TCF or the modified TCFs were eluted at a flow rate of 0.5 mL/min. from the column with a linear gradient of NaCl (up to 1.0M) and fractions of 0.5 ml were collected. The fractions containing TCF or the modified TCFs (an approximate volume of 4 mL) which were eluted with 0.7–0.8M NaCl were obtained.

3) Heparin 5-PW-FPLC

Two volumes (8 mL)of 10 mM Tris-HCl (pH 7.5) containing 0.01% Tween 20 were added to the eluate which contains TCF or the modified TCFs. This diluted solution was applied at a flow rate of 1 mL/min. to a heparin 5-PW column (0.5×7.5 cm, TOSO Co., FPLC) which had been equilibrated with approximately 20 mL of 10 mM Tris-HCl buffer (pH 7.5) containing 0.3M NaCl and 0.01% Tween 20 (buffer B). The column was washed with approximately 30 ml of buffer B. Then TCF or the modified TCFs were eluted at a flow rate of 0.5 mL/min. with a linear gradient of NaCl (up to 2.0M) and fractions of 0.5 ml were collected. The fractions containing TCF or the modified TCFs (those eluted with approximately 1.3M NaCl, a total volume of 3 mL) were obtained. These fractions were dialyzed against deionized water, lyophilized and reconstituted with phosphate-buffered saline (PBS) containing 0.001% Tween 20. The yield and the recovery of each of the final purified modified TCFs are shown in Table 1. The yields were determined with polyclonal EIA described in the following section.

TABLE 1

The yield and the recovery of each of the final purified modified TCFs

| Name | Yield(μg) | Recovery(%) |
|---|---|---|
| TCF | 2760 | 31 |
| TCF-1 | 872 | 17 |
| TCF-2 | 920 | 40 |
| TCF-3 | 253 | 16 |
| TCF-4 | 560 | 16 |
| TCF-12 | 688 | 33 |

TABLE 1-continued

The yield and the recovery of each of the final purified modified TCFs

| Name | Yield(μg) | Recovery(%) |
|---|---|---|
| TCF-13 | 1088 | 23 |
| TCF-14 | 350 | 27 |
| TCF-23 | 810 | 28 |
| TCF-24 | 648 | 19 |
| TCF-34 | 668 | 34 |
| TCF-123 | 340 | 11 |
| TCF-124 | 400 | 23 |
| TCF-134 | 187 | 22 |
| TCF-234 | 400 | 15 |
| TCF-1234 | 155 | 8 |

⑧ Quantitation of the purified modified TCFs.

1) Preparation of polyclonal antibodies and labeling of the antibodies.

Anti-TCF antiserum was obtained from rabbits which were immunized with TCF. The anti-TCF IgG was purified from the antiserum by an Affi-Gel protein A Sepharose (Bio Rad Co.) according to the manufacturer's protocol. The purified IgG was dialyzed overnight against PBS, and applied at a flow rate of 0.5 mL/min. to a TCF affinity column in which TCF was immobilized to affigel 10 (Bio Rad Co.). The immobilized column was washed with PBS and the anti-TCF IgG was eluted with 0.1M Glycine-HCl buffer (pH 2.5). The eluate was dialyzed against PBS and the purified anti-TCF polyclonal antibodies were thus obtained. The peroxydase labeled antibodies were prepared as described by Ishikawa et al. (J. Immunoassay, vol. 4, 209–327, 1983).

2) Quantitation of the purified modified TCFs.

Anti-TCF antibodies were dissolved at a concentration of 10 μg/mL in 0.1M $NaHCO_3$. The antibody solution was added (100 μL/well) to 96-well microtiter plates (NUNC Co.) and left overnight at room temperature. This step allowed the antibodies to attach to the plates. Block Ace (Snow Brand Milk Products Co. Ltd.) diluted two-fold with deionized water was added to the antibody-coated microtiter-well plates (200 μL/ml) and left for an hour at room temperature for blocking each well. The plates were then washed three times with PBS containing 0.1% Tween 20 (washing buffer). The modified TCF were diluted with appropriate volume of the first buffer (0.2M Tris-HCl pH 7.4 containing 40% Block Ace and 0.1% Tween 20) to prepare modified TCF samples. Standard TCF solution was prepared by sequentially diluting 10 ng/mL of TCF solution with the first buffer. One hundred micro liters of the modified TCF samples were added to each well, left for 3 hours at 37° C. and washed three times with the washing buffer. The Peroxydase-conjugated antibody solution was diluted 400-fold with the second buffer (0.1M Tris-HCl buffer pH 7.4 containing 20% Block Ace, 0.1% Tween 20 and 0.5 mg/mL of mouse IgG). One hundred microliters of the diluted peroxydase-labeled antibody solution was added to each well, left for 2 hours at 37° C. and washed three times with the washing buffer. Subsequently, 100 μL of substrate solution (0.4 mg/mL of o-phenylene diamine dihydrochloride and 0.006% $H_2O_2$ in 0.1M citrate-phosphate buffer, pH 4.5) was added to each well and incubated at 37° C. for 30 minutes in a dark place. The enzyme reaction was stopped by addition of 50 μL of 6N $H_2SO_4$. The absorbance at 492 nm was measured on an immuno reader (Corona Co.).

⑨ Analysis of the purified TCF or the modified TCFs on SDS-polyacrylamide gel electrophoresis.

Figure 7:
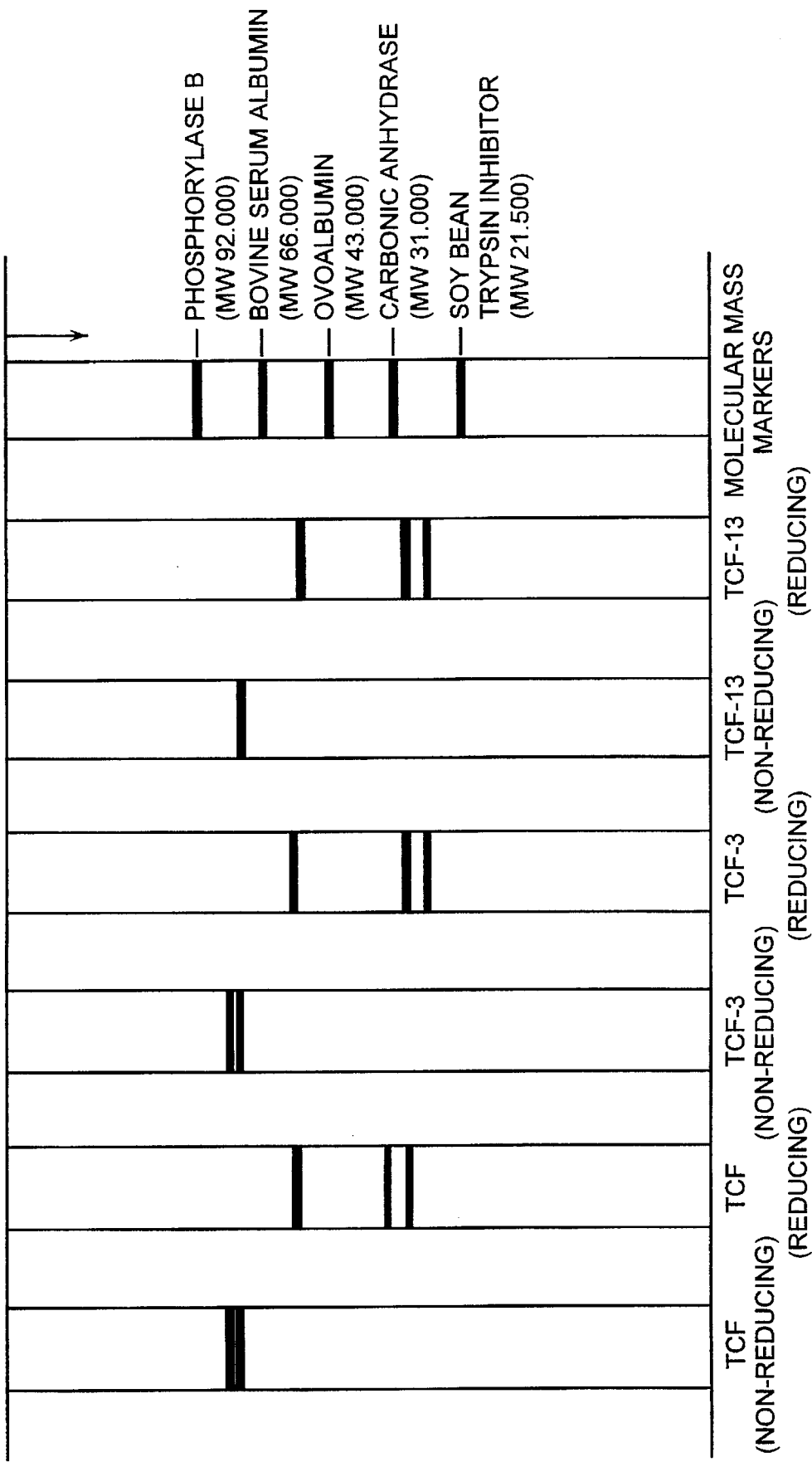
FIG. 7 shows the analysis of the representative modified TCF by SDS polyacrylamide gel electrophoresis.

Five micrograms of purified modified TCF was subjected to an SDS-polyacrylamide gel. Modified TCFs (TCF-3 and TCF-13) with prolonged biological half-lives as described later, and the wild-type TCF were applied to an SDS-polyacrylamide gel electrophoresis. The results are shown in FIG. 7. Electrophoresis was performed either in the presence (reducing conditions) or absence (non-reducing conditions) of β-mercaptoethanol. As indicated in FIG. 7 TCF showed two adjacent bands with approximate molecular masses of 78,000 and 74,000 under non-reducing conditions. The two bands of TCF-3 migrated faster than those of TCF, and the two bands of TCF-13 migrated faster than those of TCF-3, under non-reducing conditions. Under the reducing conditions, three protein bands with approximate molecular masses of 52,000, 30,000 and 26,000 were observed for TCF. Similarly, three bands with 52,000, 26,000 and 22,000 for TCF-3, and three bands with 48,000, 26,000 and 22,000 for TCF-13 were observed. The decrease in molecular mass of these modified TCFs was probably due to the removal of oligosaccharide chains. The results suggested that the desired modified TCFs were obtained. No other protein bands were detected except those deduced from the structure of the two modified proteins.

EXAMPLE 2

Biological activities of the TCF and the modified TCFs in vitro.

① Growth stimulating activity for hepatocytes.

Figure 8A:
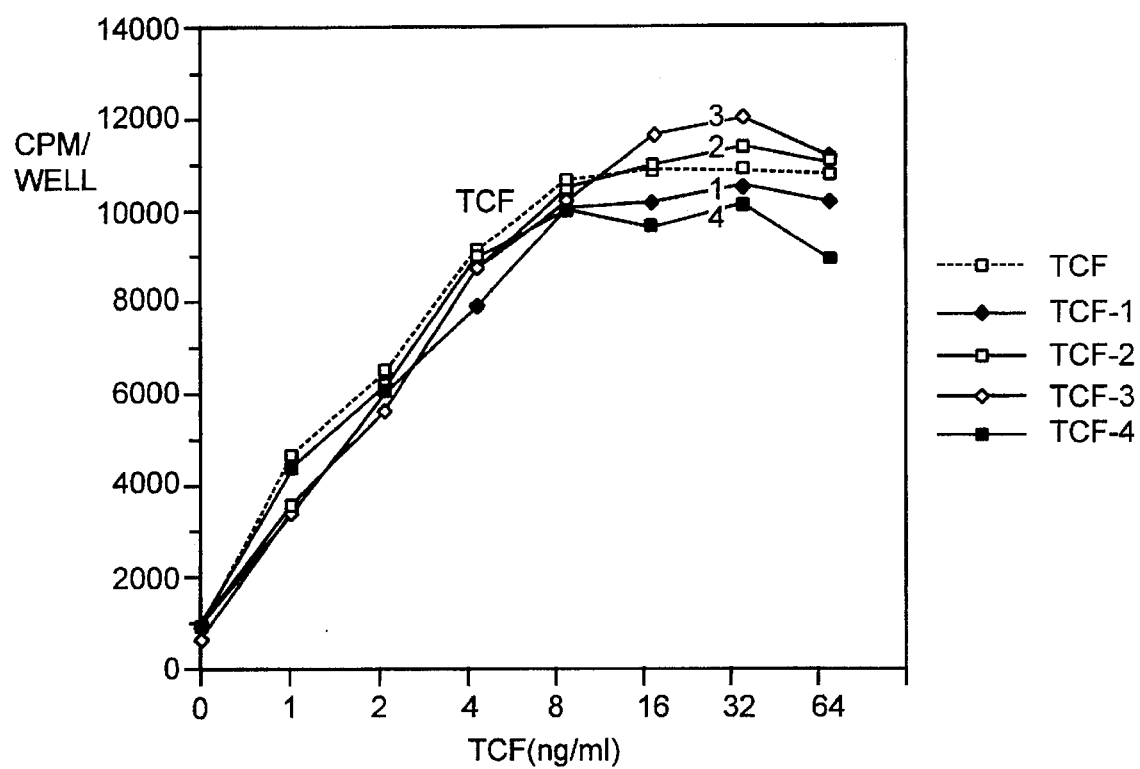
FIG. 8 shows the stimulating activities of the modified TCF for growth of hepatocytes. Each figure shows the activity of the modified TCF described below.
Figure 8B:
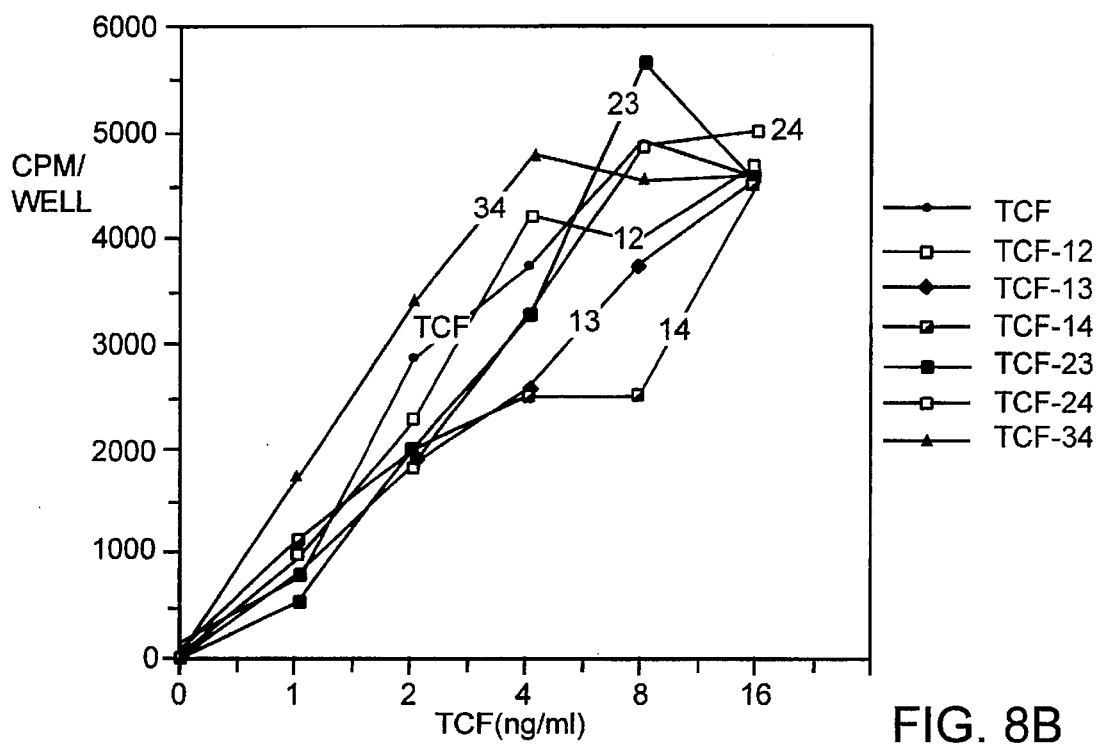
Figure 8C:
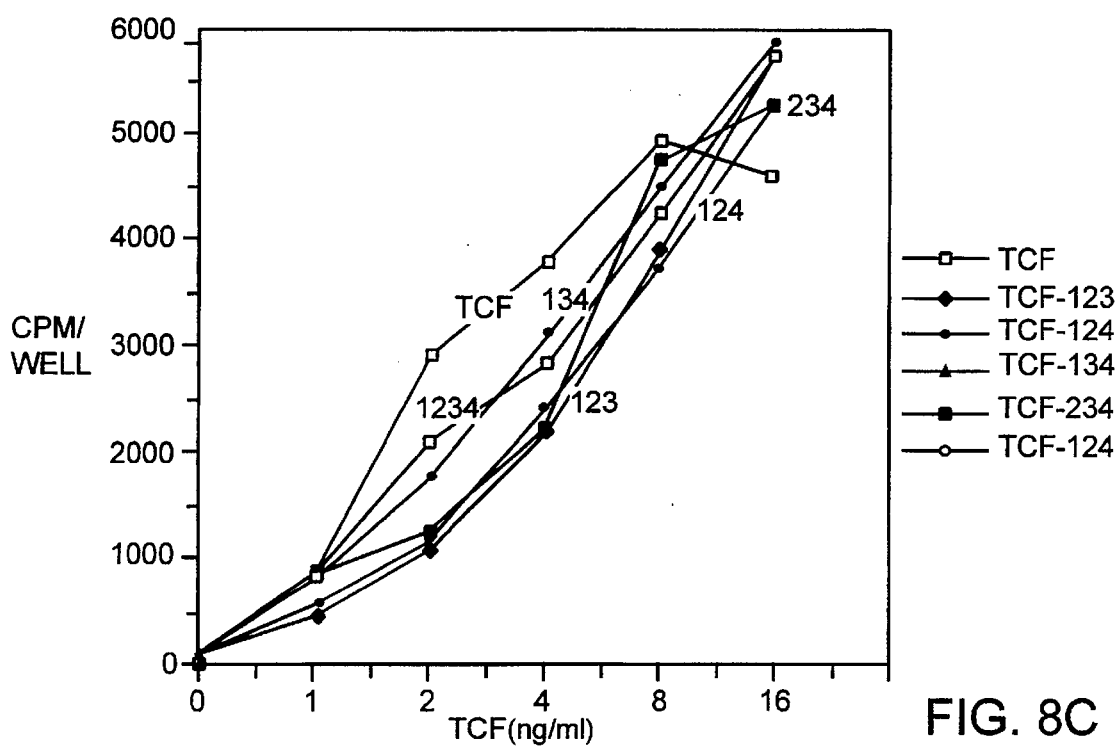

Growth stimulating activity for hepatocytes was determined as follows. Rat hepatocytes were isolated from a Wister rat (body weight was approximately 200 g) by the method of Seglen (Methods in cell biology Vol.13, p.29, Academic, Press, New York). The basal medium, Williams E (Flow laboratories Co.), containing 10% fetal bovine serum and 10 µM dexamethasone) was used for the growth of the cells. One hundred microliters of the basal medium containing $1.0 \times 10^4$ cells was added to each well in a 96-well flat-bottomed plate (Falcon Co.) and incubated at 37° C. after 24 hours of incubation, 100 µL of the basal medium containing TCF or the modified TCFs was added to each well and incubated for 22 hours at 37° C. Each well was supplemented with 1 µCi of $^3$H-thimidine (Amersham Co.) and further incubated at 37° C. for 2 hours. After washing twice with cold PBS, cells were trypsinized with 0.5% trypsine and harvested on a sheet of glass filter by a cell harvester. Radioactivities incorporated into the cells in each well were counted by Matrix 96 (Packard Co.). As shown in FIG. 8, all the modified TCFs were shown to maintain growth stimulating activities for rat hepatocytes.

② Tumor cytotoxic activity.

Tumor cytotoxic activities of TCF, TCF-3 and TCF-13 were measured. Meth A sarcoma was used as a target cell line. The cells were suspended in RPMI medium (GIBCO Co.) supplemented with 10% FCS at a final cell density of $2 \times 10^4$ cells per mL. Fifty microliters of the cell suspension was inoculated into each well in 96-well flat-bottomed microtiter plates. The purified TCF, TCF-3 and TCF-13 were serially diluted with RPMI medium from the concentration of 50 ng/mL, and the 50 µL of each diluted sample was added to each test well. After incubation at 37° C. for 5 days, MTT was added at a final concentration of 0.5 mg/ml and the plates were incubated at 37° C. Four hours later, 100 µL of the solution containing 10% SDS and 0.01M NH$_4$Cl was added to each well and left overnight at room temperature. Next day, the absorbance at 620 nm was measured as a parameter of the viable cell numbers in each well. FIG. 9 shows the results of the assay. TCF, TCF-3 and TCF-13 having cytotoxic activities to Meth A cells in a dose-dependent manner.

EXAMPLE 3

Measurement of biological half-lives of the TCF and the modified TCFs in vivo.

Anti-TCF polyclonal antibody was dissolved in 0.1M NaHCO$_3$ solution to a final concentration of 10 µg/mL. One hundred microliters of the antibody solution was added to each well and the plates were left overnight at room temperature. The wells were filled with 50% solution of Block Ace in H$_2$O, incubated for 1 hour at room temperature and washed three times with washing solution (PBS containing 0.1% Tween 20 ). Plasma samples periodically collected from the rats which were intravenously injected with TCF or the modified TCFs were diluted with normal rat serum, when necessary. TCF solutions serially diluted with normal rat serum (from 10 ng/mL) was used as the standard TCF solution. Fifty microliters of the sample solution and 50 µL of the first buffer (0.2M Tris HCl pH 7.3 containing 50% Block Ace, 0.2M NaCl, 0.1% Tween 20, 0.2% CHAPS, 20 mM Benzamidine hydrochloride, and 10 mM EDTA) was mixed and added to each well. The plates were left for 3 hours at 37° C. and washed three times with the washing buffer. One hundred microliters of the peroxidase-labeled anti-TCF antibody solution, which was 400-fold diluted with 0.1M phosphate buffer pH 7.0 containing 10% Block Ace, 0.15M NaCl, 0.1% Tween 20, 4% rat serum and 0.5% mouse IgG, was added to each well. Plates were incubated for hours at 37° C. and washed three times with the washing buffer. Subsequently, 100 µL of substrate solution (0.4 mg/mL of o-phenylene diamine dihydrochloride and 0.006% H$_2$O$_2$ in 0.1M citrate-phosphate buffer, pH 4.5) was added to each well and incubated at 37° C. for 30 minutes in a dark place. The enzyme reaction was stopped by addition of 50 µL of 6N H$_2$SO$_4$. The absorbance at 492 nm was measured on an immuno reader (Corona Co.). Thus concentrations of the TCF or the modified TCFs in rat serum were determined.

Time course of plasma levels were examined by EIA in rats after the single intravenous injection of TCF and the modified TCFs. Hale Wister rats weighing about 200 g were used. After the intravenous injection of TCF to the rats, the plasma level declined biexponentially, well described by a two-compartment model. Plasma half-lives of rapid phase and slower phase were 2.4±2.5 min.(t½β) and 15.6±4.6 min.(t½β) in rats after the TCF injection at a dose of 50 µg/kg, respectively. Plasma level profiles of modified TCF were similar to that of the wild-type TCF, but their plasma levels declined slower than that of the wild-type TCF after the intravenous injection at the same dose.

As shown in Table 2, plasma half-lives of TCF-3 and TCF-13 were prolonged and their total clearance was decreased. TCF-3 and TCF-13 had larger AUC(the area under the plasma concentration—time curve) compared to the wild-type TCF.

TABLE 2

| Pharmacokinetics parameters of the modified TCFs | | |
|---|---|---|
| SAMPLE | $t_{1/2} \alpha$ (min) | $t_{1/2} \beta$ (min) |
| TCF | 2.4 ± 0.5 | 15.6 ± 4.6 |
| TCF-1 | 2.4 ± 0.3 | 19.6 ± 0.3 |
| TCF-2 | 2.2 ± 0.6 | 18.2 ± 2.5 |
| TCF-3 | 2.9 ± 0.3 | 54.2 ± 8.3** |
| TCF-4 | 2.7 ± 0.1 | 20.6 ± 3.3 |
| TCF-12 | 2.7 ± 0.3 | 18.1 ± 1.6 |

TABLE 2-continued

Pharmacokinetics parameters of the modified TCFs

| SAMPLE | $t_{1/2}\alpha$ (min) | $t_{1/2}\beta$ (min) |
|---|---|---|
| TCF-13 | 3.8 ± 0.5** | 24.9 ± 3.1* |
| TCF-14 | 1.9 ± 0.4 | 18.8 ± 2.9 |
| TCF-23 | 2.4 ± 0.5 | 15.4 ± 0.5 |
| TCF-24 | 2.3 ± 0.1 | 16.9 ± 1.7 |
| TCF-34 | 2.2 ± 0.5 | 18.0 ± 2.1 |
| TCF-123 | 2.2 ± 0.1 | 17.2 ± 0.8 |
| TCF-124 | 2.3 ± 0.1 | 15.7 ± 2.7 |
| TCF-134 | 2.3 ± 0.4 | 19.1 ± 3.2 |
| TCF-234 | 2.6 ± 0.6 | 16.8 ± 1.6 |
| TCF-1234 | 2.9 ± 0.1* | 24.2 ± 5.5* |

Mean ± SD
Significantly difference from Wild-type TCF (*$P < 0.05$, **$P < 0.01$)

TABLE 3

Pharmacokinetics parameters of the modified TCFs

| SAMPLE | AUC (ng · min/ml) | $CL_{total}$ (ml/min/kg) |
|---|---|---|
| TCF | 1030.0 ± 257.9 | 51.5 ± 13.9 |
| TCF-1 | 811.6 ± 158.3 | 63.2 ± 12.2 |
| TCF-2 | 1143.7 ± 551.7 | 49.8 ± 18.9 |
| TCF-3 | 2679 ± 292.1** | 18.8 ± 2.1** |
| TCF-4 | 897.8 ± 263.5 | 58.6 ± 14.7 |
| TCF-12 | 1246.4 ± 290.8 | 41.7 ± 10.6 |
| TCF-13 | 8301.0 ± 299.7** | 6.0 ± 0.2** |
| TCF-14 | 972.5 ± 162.2 | 52.5 ± 9.5 |
| TCF-23 | 1223.0 ± 356.7 | 43.6 ± 14.3 |
| TCF-24 | 1017.8 ± 210.0 | 51.0 ± 8.3 |
| TCF-34 | 983.0 ± 61.0 | 51.0 ± 3.2 |
| TCF-123 | 963.8 ± 66.2 | 52.0 ± 3.5 |
| TCF-124 | 1126.3 ± 265.0 | 45.9 ± 9.5 |
| TCF-134 | 960.9 ± 279.7 | 55.2 ± 16.7 |
| TCF-234 | 892.9 ± 119.7 | 56.6 ± 7.1 |
| TCF-1234 | 1266.5 ± 78.9 | 39.6 ± 2.6 |

Mean ± SD
Significantly difference from Wild-type TCF (*$P < 0.05$, **$P < 0.01$)

These results indicated that TCF-3 and TCF-13 had slower metabolic fates and have larger bioavailabilities than those of the wild-type TCF. The amino acid sequence of TCF-3 discloses in Seq Id No. 2, and the sequence of TCF-13 discloses in Seq Id No. 3.

The modified TCFs in the present invention have longer biological half-lives, maintaining growth stimulating activities for hepatocytes and cytotoxic activities to tumor cells, and are therefore useful as therapeutic agents for liver diseases or as anti-cancer drugs.

REFERENCE OF MICROORGANISM (1) pcTCF(S)/MC1061/P3
 Organization of Deposition:
 National Institute of Bioscience and Human-Technology,
 Agency of Industrial Science and Technology,
 Ministry of International Trade and Industry
 Address:
 1–3, Higashi 1 chome, Tsukuba-shi, Ibaraki-ken, Japan
 Deposition Number:
 FERM BP-3479

(2) pBPV-TCF-3
 Organization of Deposition:
 National Institute of Bioscience and Human-Technology,
 Agency of Industrial Science and Technology,
 Ministry of International Trade and Industry
 Address:
 1–3, Higashi 1 chome, Tsukuba-shi, Ibaraki-ken, Japan
 Deposition Number:
 FERM BP-4454

(3) pBPV-TCF-13
 Organization of Deposition:
 National Institute of Bioscience and Human-Technology,
 Agency of Industrial Science and Technology,
 Ministry of International Trade and Industry
 Address:
 1–3, Higashi 1 chome, Tsukuba-shi, Ibaraki-ken, Japan
 Deposition Number:
 FERM BP-4455

We claim:

1. A modified TCF comprising TCF having a deletion of one or more oligosaccharide chains, said modified TCF having an amino acid sequence wherein at least one of the amino acid residues responsible for binding N-linked oligosaccharide chains is modified such that at least one of the N-linked oligosaccharide chains is prevented from binding to the modified TCF, wherein the amino acid residues responsible for binding the N-linked oligosaccharide chains are selected from the group consisting of asparagine, threonine and serine.

2. The modified TCF of claim 1 wherein the amino acid sequence is Sequence ID No. 2 or Sequence ID No. 3.

3. The modified TCF of claim 1 wherein at least one of the amino acid residues responsible for binding N-linked oligosaccharide chains is replaced such that at least one of said chains is prevented from binding to at least one Asn residue in Sequence ID No. 1.

4. The modified TCF of claim 3 wherein the Asn residue is selected from the group consisting of: Asn residue at position 289, 397, 561, and 648 in Sequence ID No. 1.

5. The modified TCF of claim 1 wherein Ala is the amino acid residue at position 563 as depicted in Sequence ID No. 2.

6. The modified TCF of claim 1 wherein Gln is the amino acid residue at position 289 and Ala is the amino acid residue at position 563 as depicted in Sequence ID No. 3.

7. A modified TCF produced by expression of a DNA encoding the amino acid sequence of Sequence ID No. 2.

8. A modified TCF produced by expression of DNA encoding the amino acid sequence of Sequence ID No. 3.

9. A DNA sequence encoding modified TCF having a deletion of one or more oligosaccharide chains, said DNA sequence comprising a nucleic acid sequence encoding an amino acid sequence wherein at least one of the amino acid residues responsible for binding N-linked oligosaccharide chains is modified such that at least one of the N-linked oligosaccharide chains is prevented from binding to the modified TCF, wherein the amino acid residues responsible for binding the N-linked oligosaccharide chains are selected from the group consisting of asparagine, threonine and serine.

10. The DNA sequence of claim 9 wherein the amino acid sequence is Sequence ID No. 2 or Sequence I.D. No. 3.

11. The DNA sequence of claim 9 wherein the nucleic acid sequence encoding the amino acid sequence responsible for binding N-linked oligosaccharides chains is modified such that at least one of said chains is prevented from binding to at least one Asn residue in the amino acid sequence encoded by Sequence I.D. No. 4.

* * * * *